(12) United States Patent
Osypka et al.

(10) Patent No.: US 8,116,875 B2
(45) Date of Patent: Feb. 14, 2012

(54) IMPLANTABLE NEUROSTIMULATION SYSTEMS

(75) Inventors: Thomas P. Osypka, Palm Harbor, FL (US); Hyoung-Ihl Kim, Jeonbug (KR); Yong-Il Shin, Iksan (KR)

(73) Assignee: Neuropoint Medical, Inc., Palm Harbor, FL (US)

( * ) Notice: Subject to any disclaimer, the term of this patent is extended or adjusted under 35 U.S.C. 154(b) by 991 days.

(21) Appl. No.: 11/818,728

(22) Filed: Jun. 15, 2007

(65) Prior Publication Data

US 2008/0004676 A1    Jan. 3, 2008

Related U.S. Application Data

(60) Provisional application No. 60/814,617, filed on Jun. 16, 2006.

(51) Int. Cl.
*A61N 1/05* (2006.01)
(52) U.S. Cl. .......................... 607/45; 607/139
(58) Field of Classification Search ............ 607/45, 607/48, 139
See application file for complete search history.

(56) References Cited

U.S. PATENT DOCUMENTS

| | | | |
|---|---|---|---|
| 6,066,163 A * | 5/2000 | John | 607/45 |
| 6,128,537 A * | 10/2000 | Rise | 607/45 |
| 6,482,182 B1 * | 11/2002 | Carroll et al. | 604/174 |
| 7,010,351 B2 | 3/2006 | Firlik et al. | |
| 7,107,097 B2 | 9/2006 | Stern et al. | |
| 7,146,217 B2 | 12/2006 | Firlik et al. | |
| 2003/0187490 A1 * | 10/2003 | Gliner | 607/116 |
| 2004/0102828 A1 * | 5/2004 | Lowry et al. | 607/116 |
| 2005/0070971 A1 * | 3/2005 | Fowler et al. | 607/45 |
| 2005/0240242 A1 * | 10/2005 | DiLorenzo | 607/45 |
| 2006/0116743 A1 * | 6/2006 | Gibson et al. | 607/57 |

FOREIGN PATENT DOCUMENTS

| | | |
|---|---|---|
| WO | WO 2004/050175 A1 | 6/2004 |
| WO | WO 2005/011805 A2 | 2/2005 |
| WO | WO 2006/019766 A2 | 2/2006 |

* cited by examiner

*Primary Examiner* — Carl H Layno
*Assistant Examiner* — Luther Behringer
(74) *Attorney, Agent, or Firm* — Scott D. Wofsy; Edwards Wildman Palmer LLP

(57) ABSTRACT

New and useful neurostimulation systems are provided that include an implantable pulse generator dimensioned and configured for implantation in the skull of a patient. The implantable pulse generator has an electrode operatively associated with a distal end portion thereof and can be provided with adjustment means, such as an adjustable biasing member or spring arranged between the electrode to the distal end portion of the pulse generator. Also provided are systems involving networked neurostimulators that are configured and adapted to work jointly in accordance with prescribed treatment protocol to effect a desired recovery from brain injury. Such networked neurostimulation systems are particularly advantageous for effecting relatively large and/or relatively distant regions of the brain. Additionally, systems and methods for motor-evoked potential (MEP)-based neuromodulation are provided. Further, AC and/or DC stimulation can be utilized, depending on the precise implementation.

35 Claims, 23 Drawing Sheets

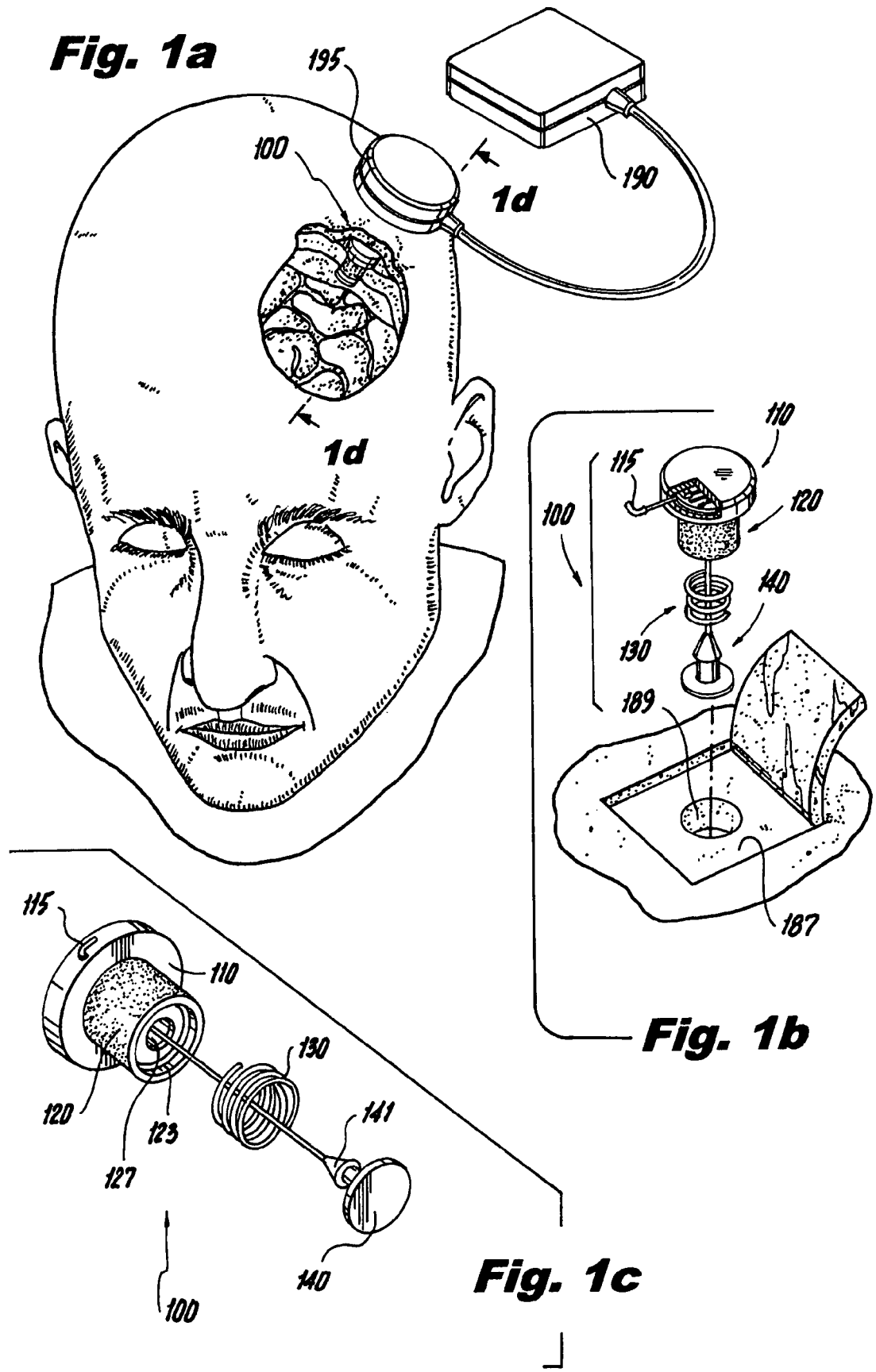

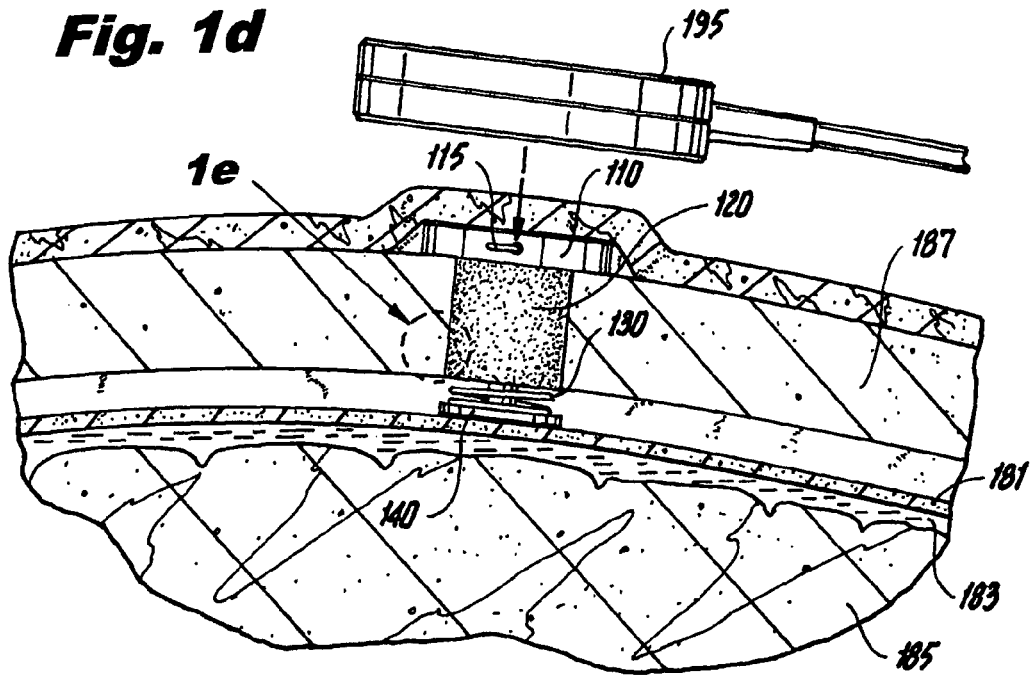
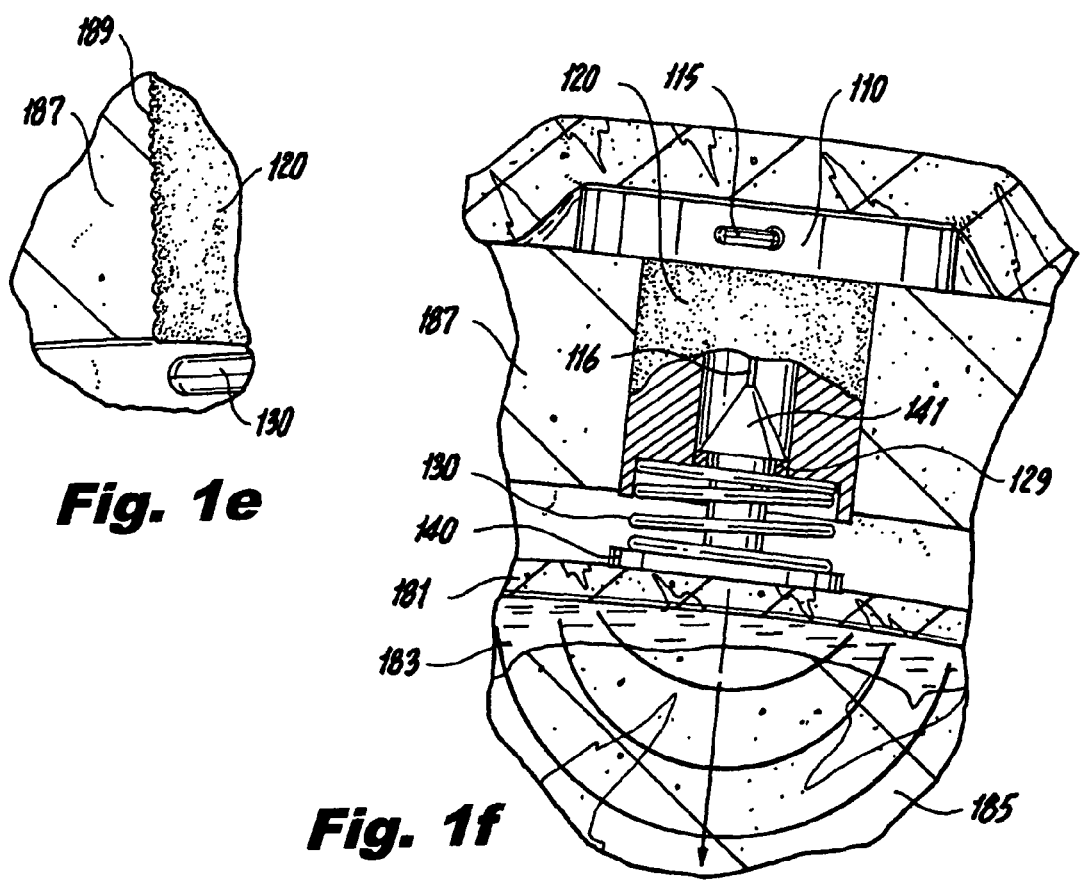

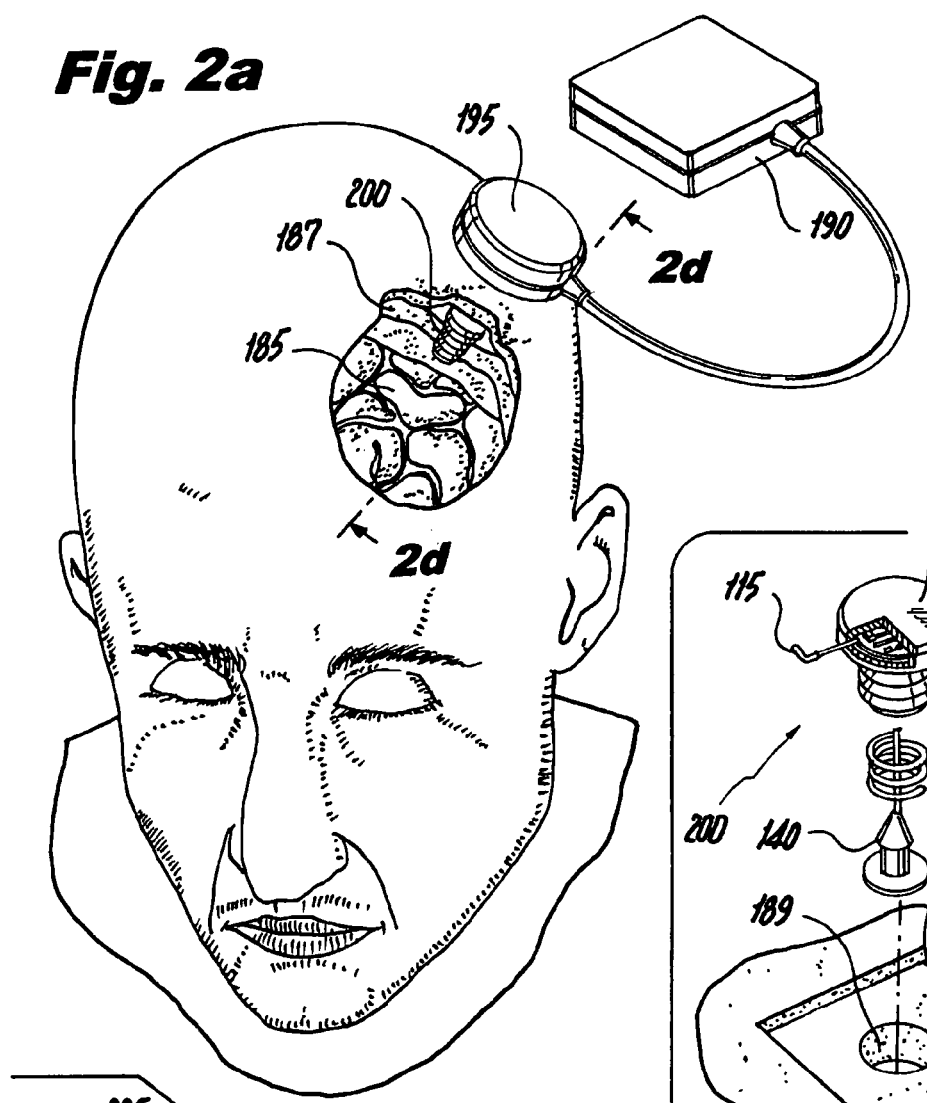
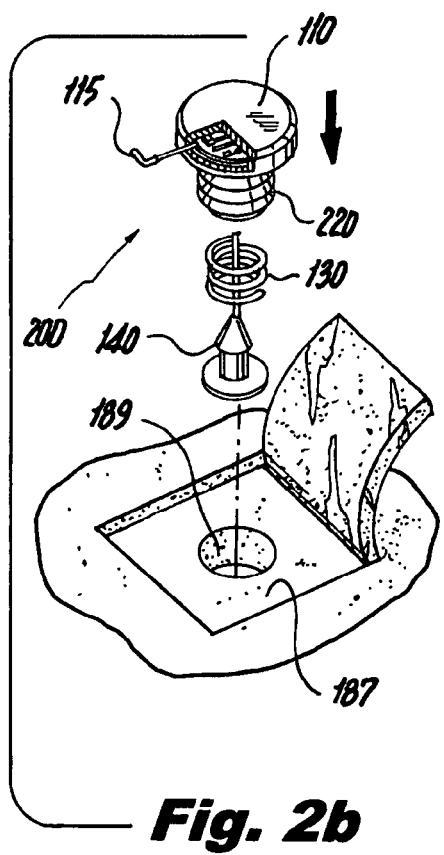
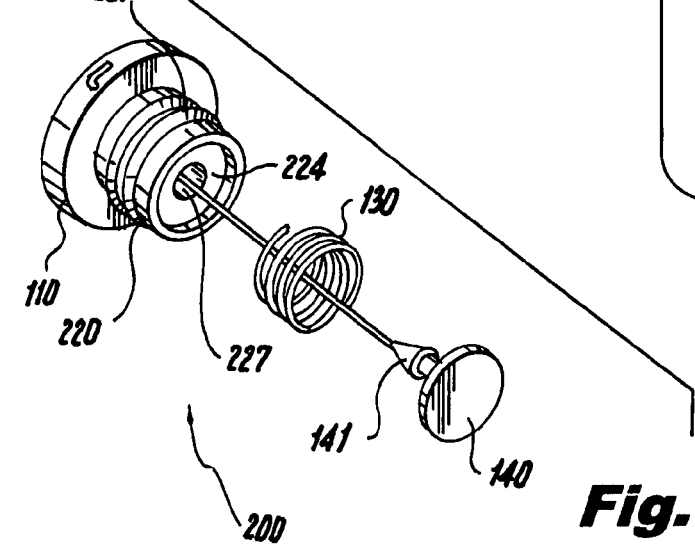
Fig. 2a
Fig. 2b
Fig. 2c

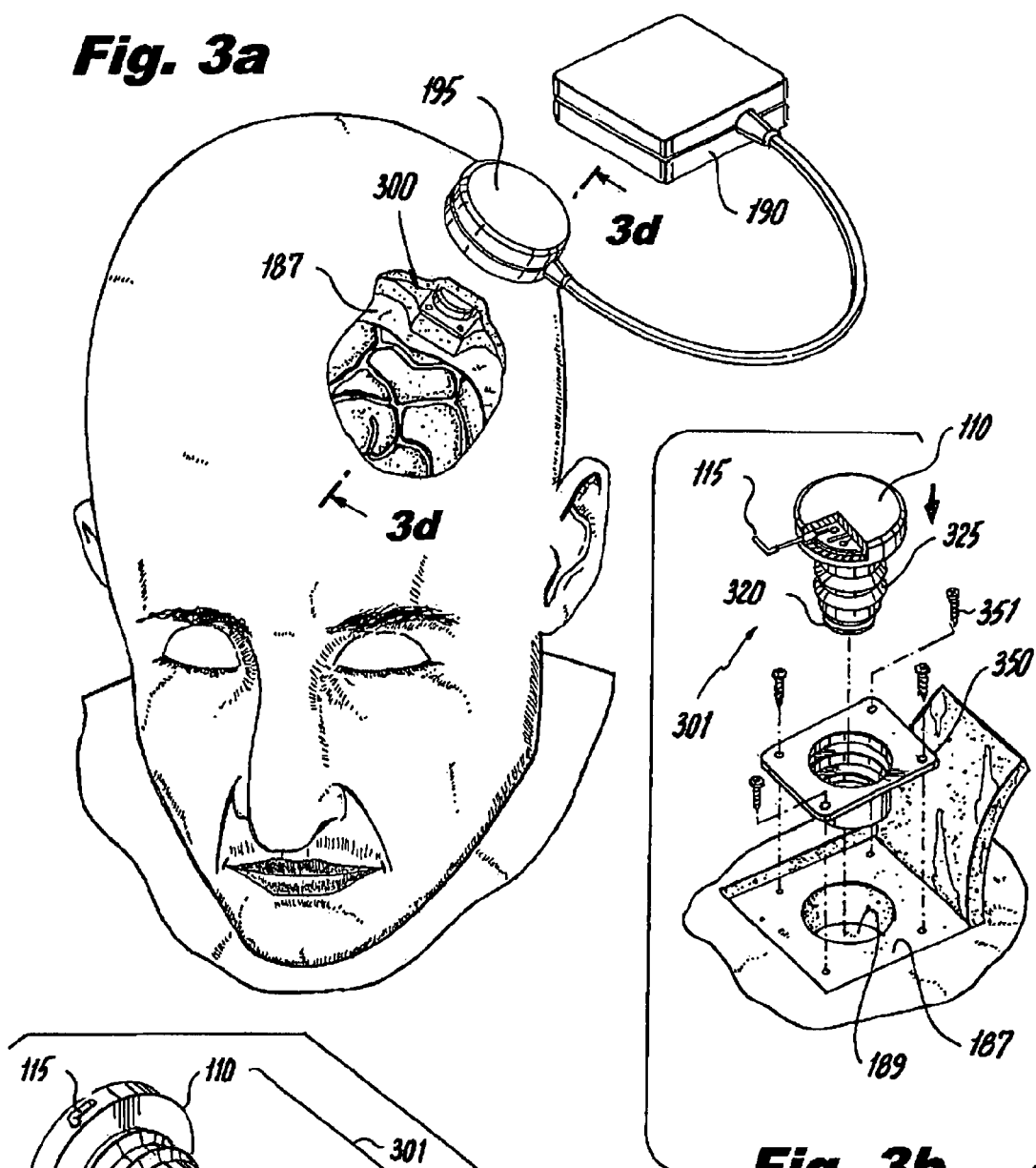
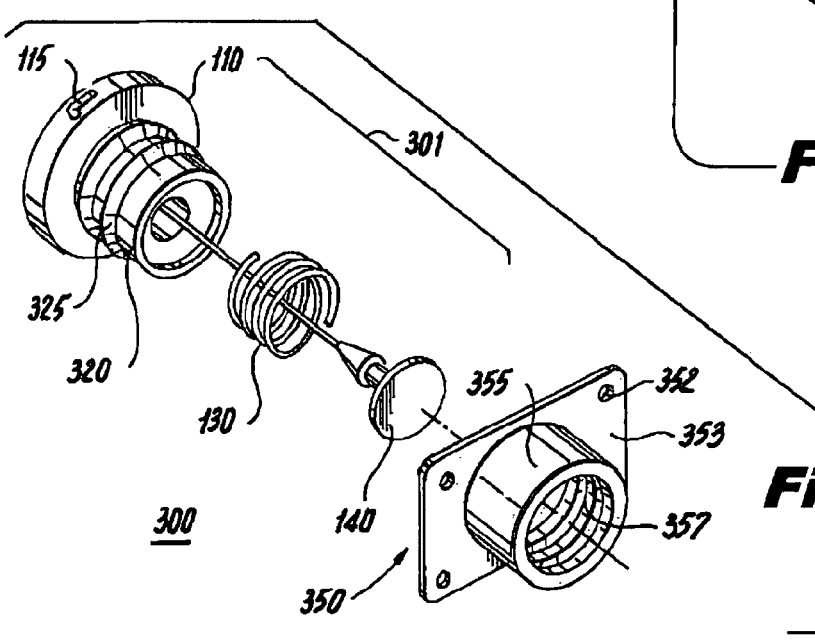

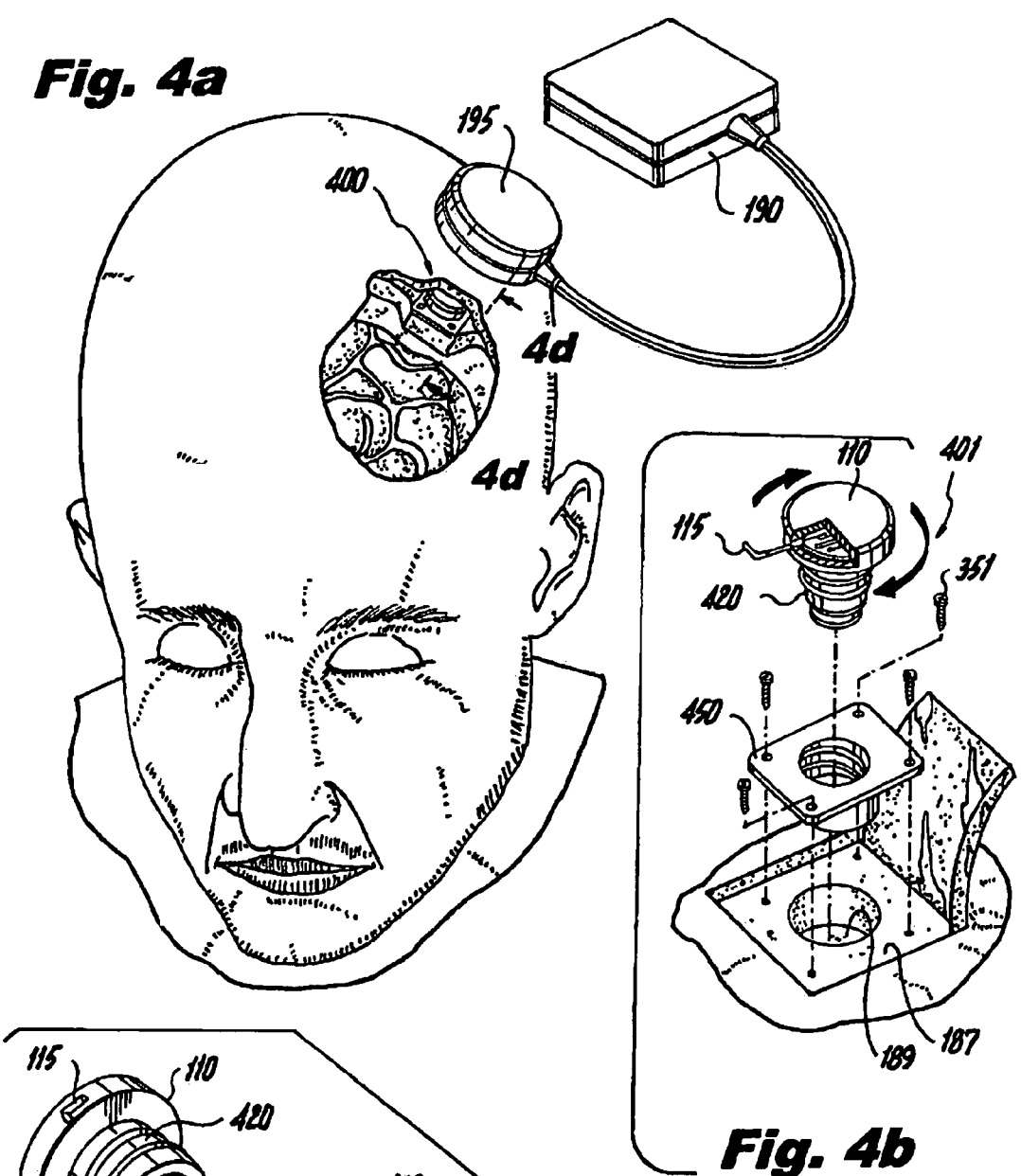
*Fig. 4a*
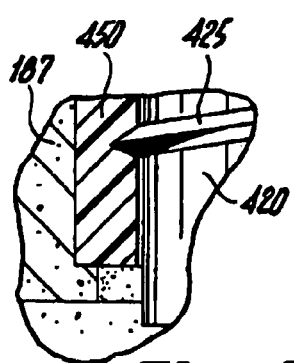
*Fig. 4b*
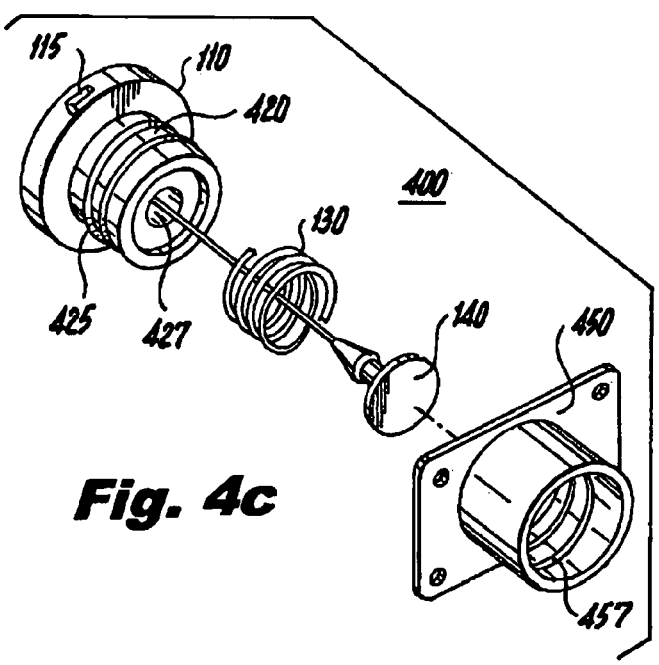
*Fig. 4c*
*Fig. 4d*

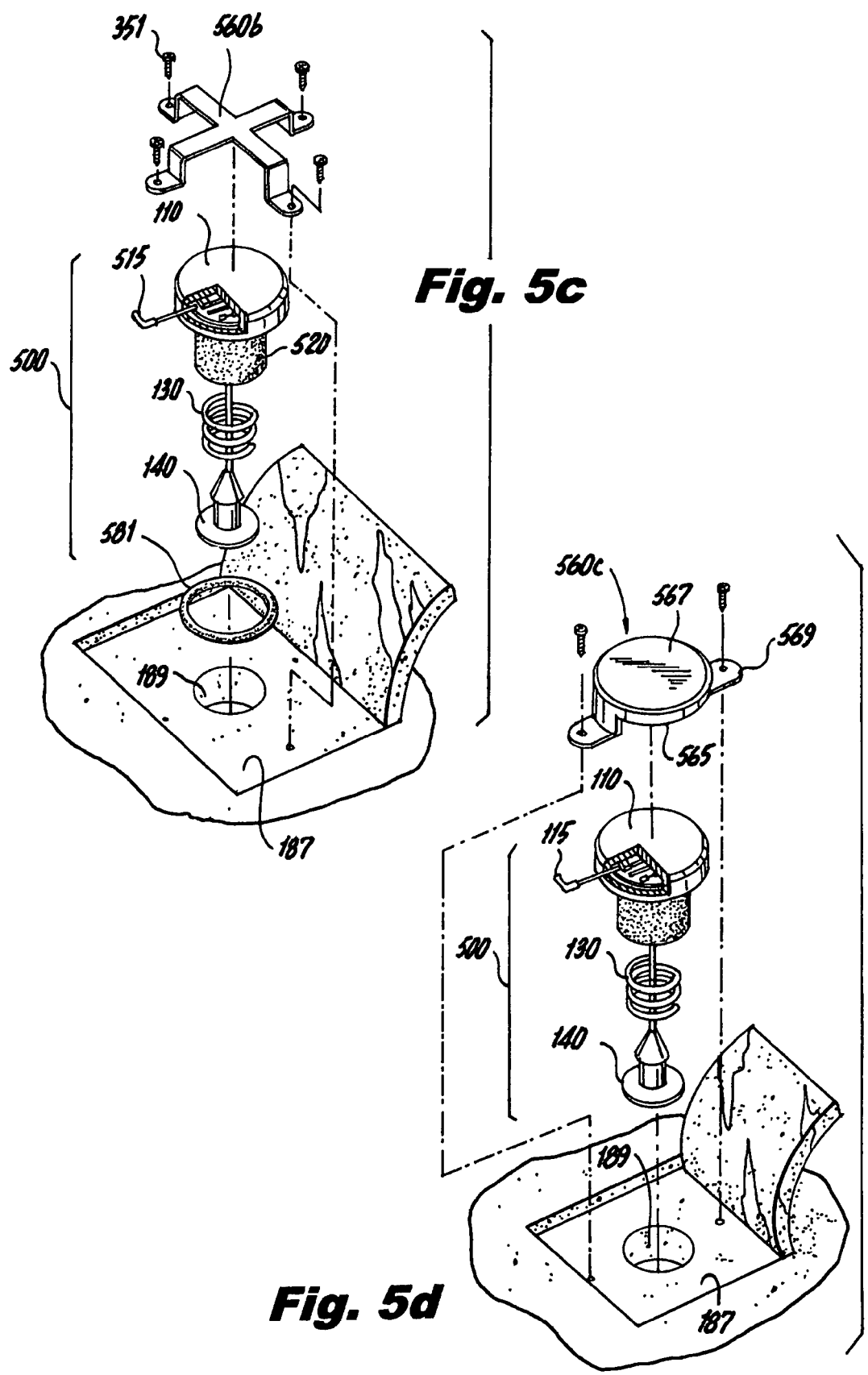

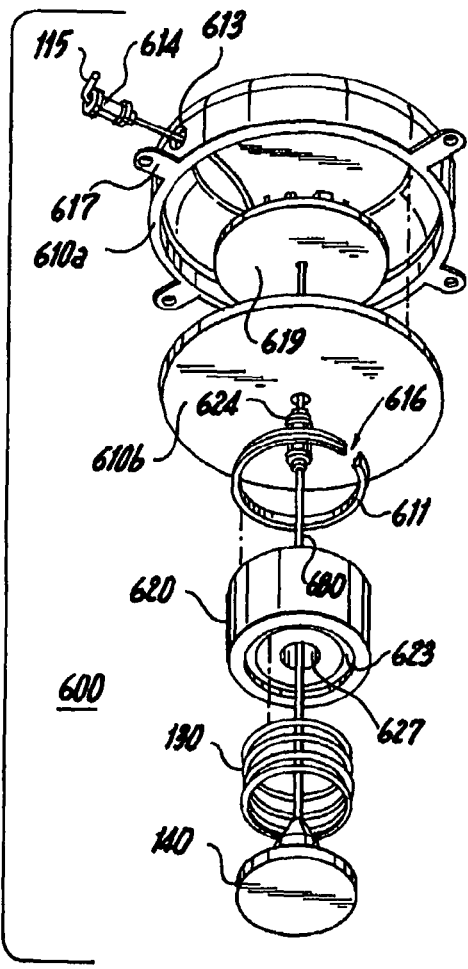
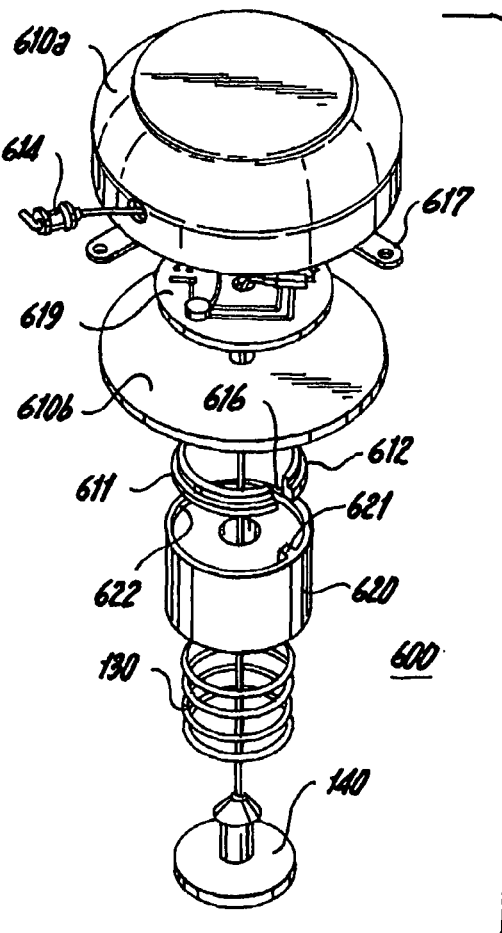
Fig. 6c
Fig. 6d
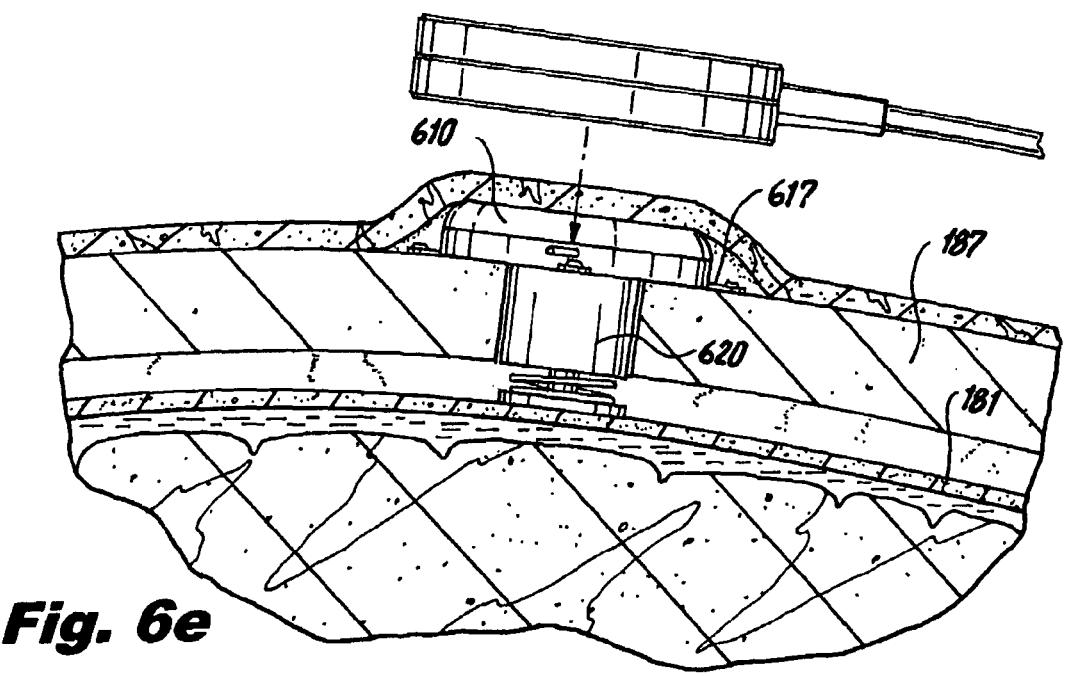
Fig. 6e

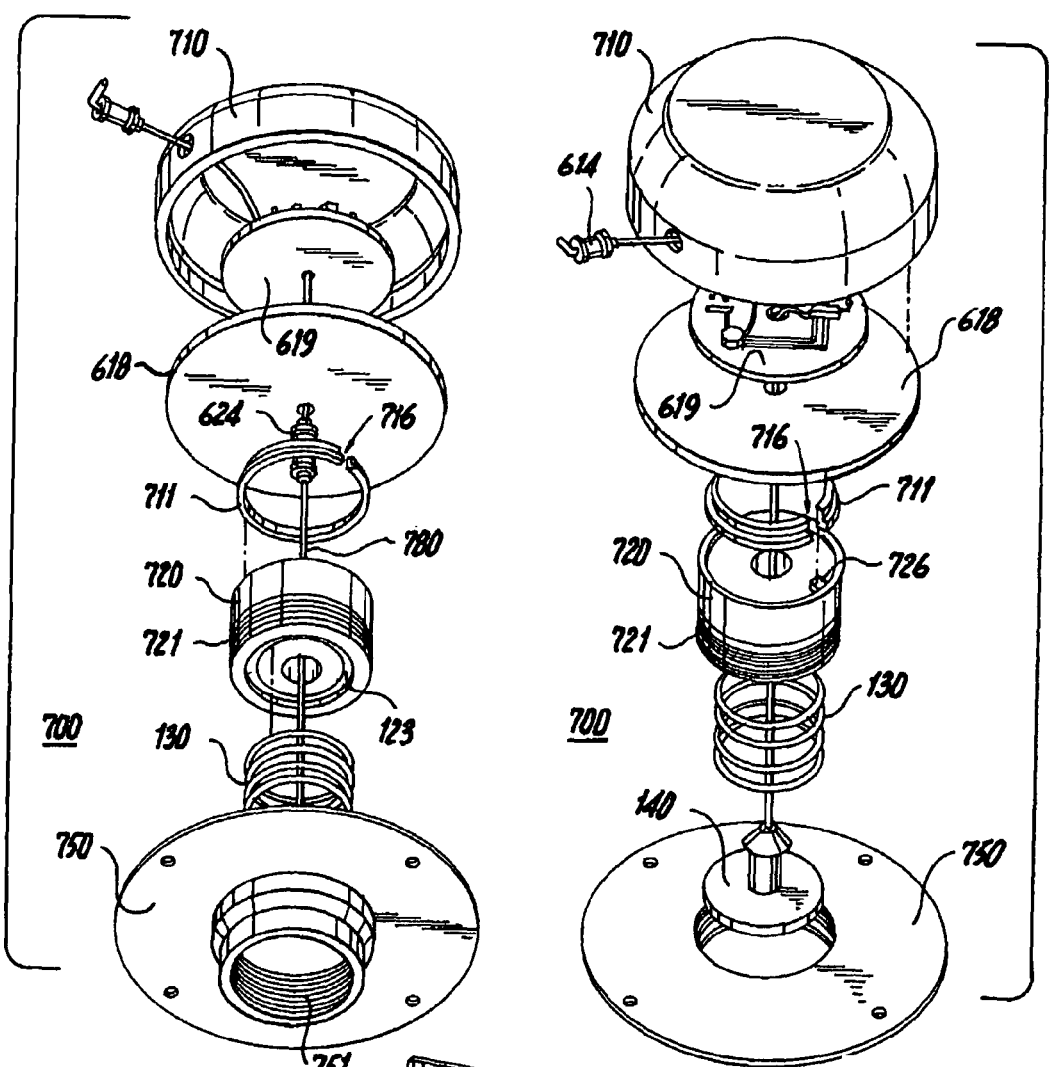
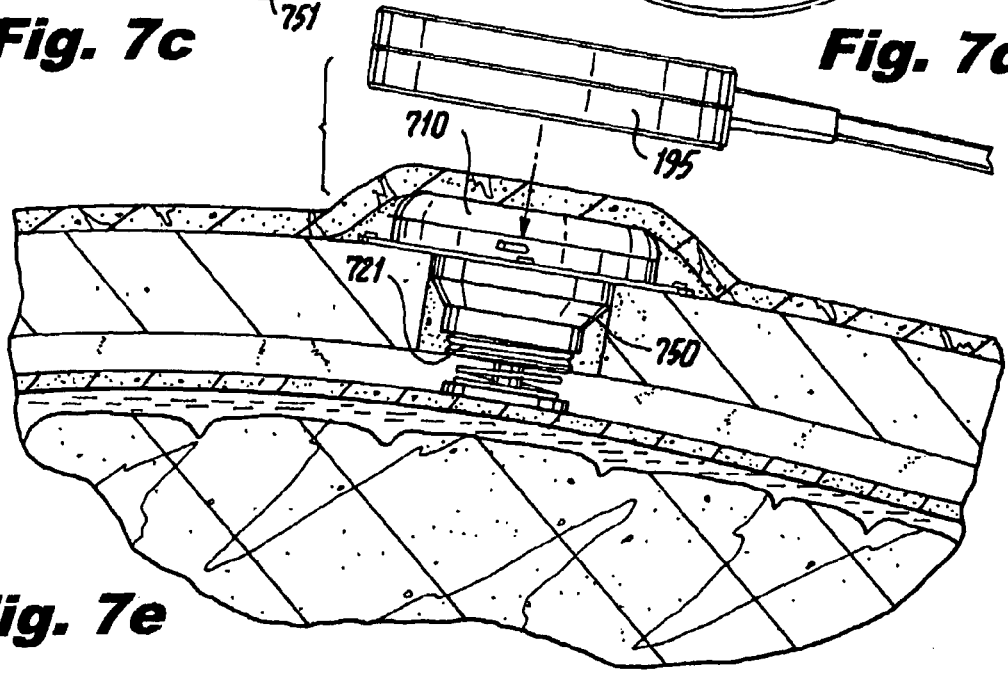
Fig. 7c  Fig. 7d
Fig. 7e

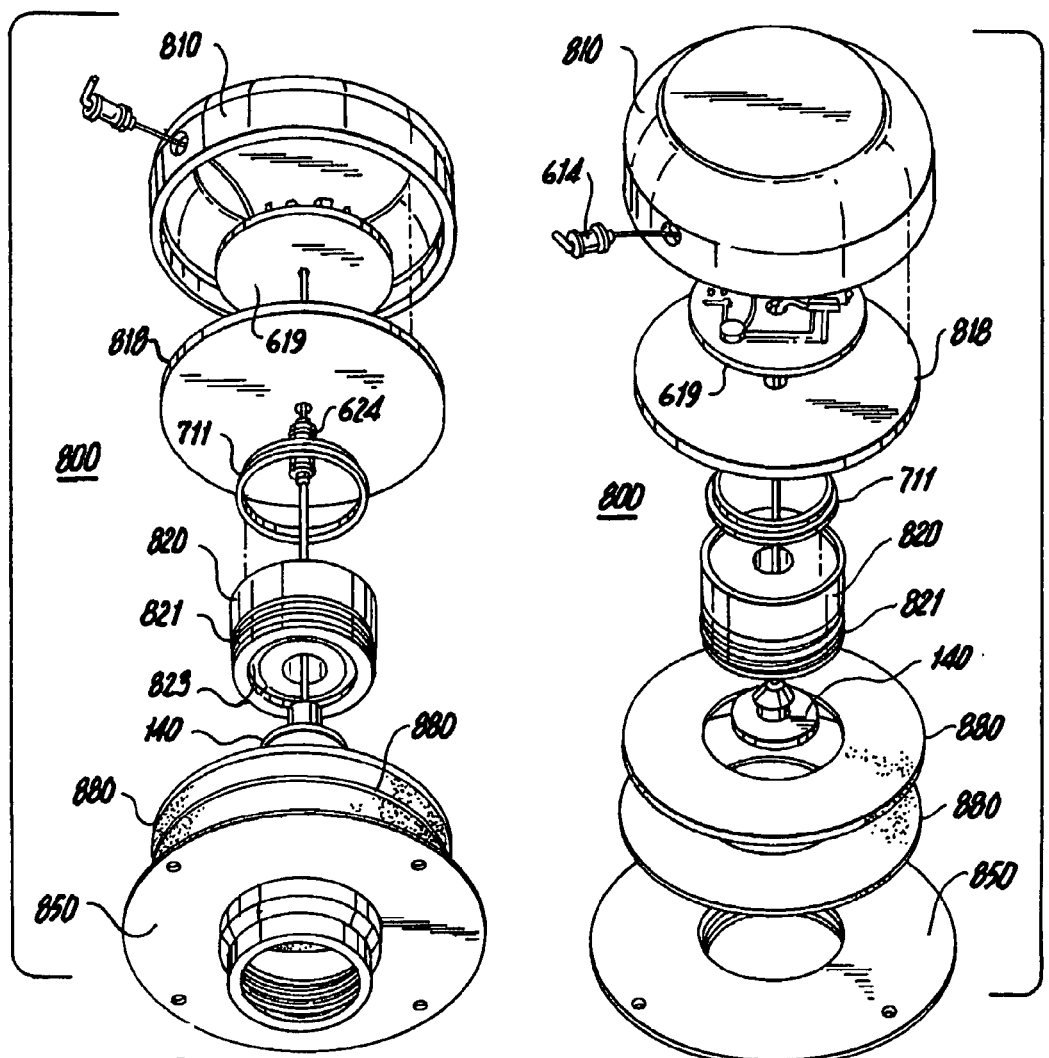
Fig. 8c
Fig. 8d
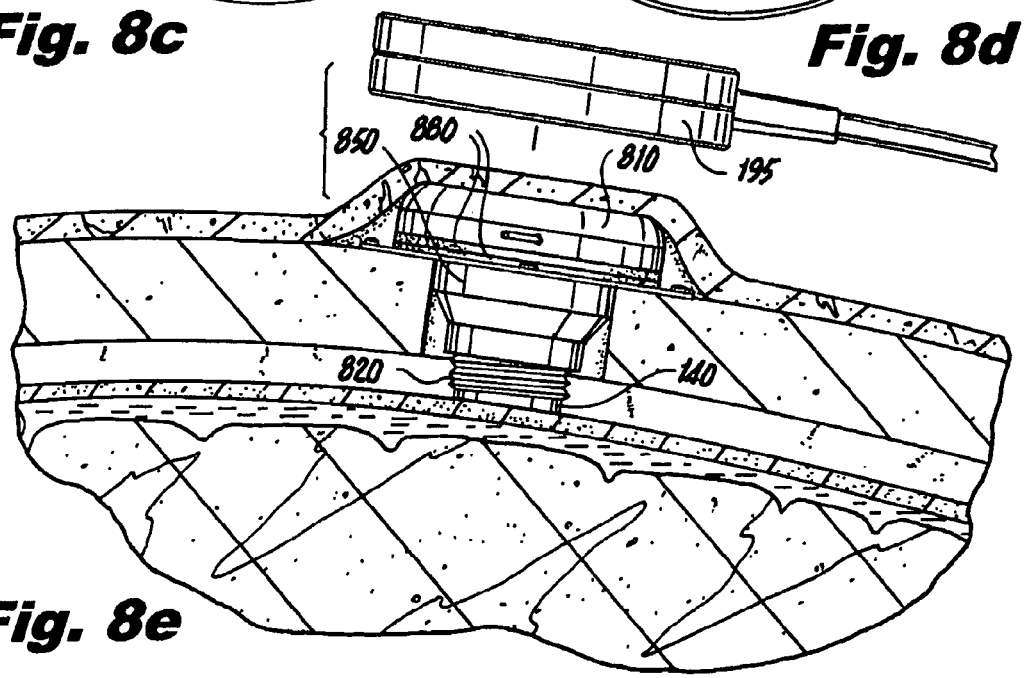
Fig. 8e

IMPLANTABLE NEUROSTIMULATION SYSTEMS

CROSS-REFERENCE TO RELATED APPLICATIONS

This application claims priority under 35 U.S.C. §119 to U.S. Provisional Patent Application Ser. No. 60/814,617, filed Jun. 16, 2006, which is hereby incorporated by reference in its entirety.

BACKGROUND OF THE INVENTION

1. Field of the Invention

The subject invention is directed to an implantable stimulation system, and more particularly, to a new and useful implantable neurostimulator for stimulating the cerebral cortex of the brain. The subject invention is also directed to such stimulations systems that include networked neurostimulators.

2. Description of Related Art

The cerebral cortex is the outer layer of gray matter in the cerebrum. It consists mainly of neuronal cell bodies and dendrites, and is associated with higher functions, including language and abstract thought. The cerebral cortex is 2-4 mm (0.08-0.16 inches) thick and is folded. The dura mater is the dense fibrous tissue covering of the brain. It extends between the cerebral hemisphere as the falx cerebri.

Current neurostimulation systems for stimulating the cerebral cortex of the brain include a conductive lead having an electrode at one end for implantation adjacent the dura mater and a connector at the other end for engaging the header of a pulse generator. The pulse generator is typically implanted at location remote from the stimulation site. Additionally, current neurostimulation systems include neurostimulators that are not capable of working in unison to effect large and/or distant parts of the brain, and which are only capable of using AC (alternating-current) stimulation.

SUMMARY OF THE INVENTION

The subject invention is directed to new and useful neurostimulation systems that include an implantable pulse generator dimensioned and configured for implantation in the skull of a patient. The implantable pulse generator has an electrode operatively associated with a distal end portion thereof and can be provided with adjustment means, such as an adjustable biasing member or spring arranged between the electrode to the distal end portion of the pulse generator. The proximal end portion of the pulse generator is disposed beneath the scalp and can be adapted and configured to serve as a receiver for communicating with an external programming device designed to control the operation of the pulse generator.

The subject invention is also directed to systems involving networked neurostimulators that are configured and adapted to work jointly in accordance with prescribed treatment protocol to effect a desired recovery from brain injury. Such networked neurostimulation systems are particularly advantageous for effecting relatively large and/or relatively distant regions of the brain that are functionally related.

In accordance with the invention, an implantable neurostimulator is provided having a housing, mounting means for securing the housing and the neurostimulator to a cranium of a patient and a stimulus generating means provided within the housing for generating a therapeutic electrical stimulus. The neurostimulator further includes a first electrode for contacting a dura of a brain of the patient, an electrically conductive element operatively connecting the pulse generating means and the electrode, adapted and configured to deliver the electrical stimulus generated by the pulse generating means to the electrode, and a stem element arranged between the housing and the electrode, a length of the stem setting a minimum distance between the housing and the electrode.

The implantable neurostimulator can further include an antenna operatively connected to the pulse generating means, the pulse generating means receiving a control signal from an external control unit through the antenna.

Additionally, biasing means can be arranged between the mounting means and the electrode for biasing the electrode toward the brain of the patient. The biasing means can be arranged between the housing and the electrode. The biasing means can be a resilient element, such as a spring. Further, the biasing means can function as an electrically conductive element by having at least an electrically conductive portion. Alternatively or additionally, the biasing means can be one or more shims.

The mounting means can be integrally formed with the housing, and can include one or more extension portions extending from the housing, adapted and configured to be secured to the cranium of the patient by one or more mechanical fasteners. Further, the mounting means can be integrally formed with the stem element, the stem element directly engaging the cranium of the patient. The mounting means can include threads arranged on an outer surface of the stem element for engaging the cranium of the patient. Alternatively, the mounting means can include a textured surface arranged on an outer surface of the stem element for engaging the cranium of the patient. Such textured surface can be adapted and configured to promote bone ingrowth into the neurostimulator, to aid fastening of the neurostimulator to the cranium.

Additionally or alternatively, the mounting means can include a fastening strap configured and adapted to engage the housing and to be secured to the cranium of the patient by one or more mechanical fasteners. Further, the mounting means can include a platform element configured and adapted to be secured to the cranium of the patient by one or more mechanical fasteners, to which the stem element is also mutually engageable. Additionally, the housing can be adapted to engage the platform element.

In accordance with the invention, the stem element can function as the electrically conductive element by having at least an electrically conductive portion.

The housing can include a cap portion and a base portion sealed together, forming the housing. The neurostimulator can further include a retainer lip arranged on a lower surface of the housing, adapted and configured to engage the stem element. The retainer lip can include an anti-rotation feature to inhibit relative rotation between the retainer lip and the stem element. Further, the housing can be adapted and configured to function as a second electrode, to complete an electrical circuit with the first electrode when delivering a therapeutic electrical stimulus. Alternatively, the housing can be provided with a separate second electrode, carried thereon, to complete an electrical circuit with the first electrode when delivering a therapeutic electrical stimulus.

In accordance with the invention, the first electrode can be adapted and configured to slideably engage the stem element, a biasing element being provided between the electrode and stem element for urging the first electrode toward the brain of the patient. The stem element can be provided with a groove for engaging the biasing element, to prevent unintentional relative translation between the stem element and the biasing element.

In accordance with the invention, an aperture can be defined in the housing, configured and adapted to receive passage of an antenna, extending from the stimulus generating means outside of the housing. Further, a feedthrough element can be provided within the aperture to seal an internal environment of the housing from the external environment of the housing. Alternatively or additionally, an aperture can be defined in the housing, configured and adapted to receive passage of a conductor, extending from the stimulus generating means to the first electrode.

In accordance with another aspect of the invention, a system for therapeutic neurostimulation is provided that includes a plurality of implantable neurostimulators as set forth herein and/or separate electrodes, and communication means connecting the plurality of neurostimulators and/or electrodes. The plurality of implantable neurostimulators and/or electrodes can be arranged in an array in the cranium of the patient. The array can be a rectangular or circular array, for example. The plurality of implantable neurostimulators and/or electrodes can be adapted and configured to communicate with one another by way of a conductive element, such as a conductive lead provided between implantable neurostimulators and/or electrodes. Alternatively or additionally, the neurostimulators can be adapted and configured to communicate with one another by way of a wireless signal, such as but not limited to bluetooth, Wi-Fi or other RF signal. In accordance with this aspect of the invention, at least one implantable neurostimulator and/or electrode can be adapted and configured to receive power from at least one other implantable neurostimulator by way of a conductive element, such as a lead, provided between implantable neurostimulators. In accordance with this aspect or other aspects of the invention, a programmer can be provided external to the patient for programming a predetermined treatment protocol into at least one implantable neurostimulator.

In accordance with another aspect of the invention, a method for using motor evoked potential (MEP) for determination of optimal treatment parameters is provided. The method can include the steps of
  a) implanting a primary stimulating electrode in a target region of the brain cortex, in which treatment is desired;
  b) implanting a satellite stimulating electrode arranged on the motor cortex of the patient's brain;
  c) stimulating the motor cortex a first time by way of the satellite stimulating electrode and measuring a motor evoked potential (MEP) at a muscle corresponding to the stimulated region of the motor cortex;
  d) stimulating the target region of the brain by way of the primary stimulating electrode;
  e) stimulating the motor cortex a second time by way of the satellite stimulating electrode and measurement of motor evoked potential (MEP) at the muscle corresponding to the stimulated region of the motor cortex;
  f) comparing the cortical excitability between the first motor cortex stimulation and the second motor cortex stimulation;
  g) determining optimal treatment parameters based on the compared cortical excitability; and
  h) stimulating the target region by way of the primary stimulating electrode for a treatment duration.

The method can further include repeating of steps c through g during or after a prescribed course of treatment.

In accordance with the invention, AC (alternating current) or DC (direct current) can be used. For instance, in cases such as epilepsy or Parkinson's disease, in which brain excitability increases, high frequency AC stimulation or cathodal DC stimulation is effective in reducing the excitability. On the other hand, as in cases of stroke, where brain excitability decreases, facilitatory AC stimulation or anodal DC stimulation is effective. DC stimulation advantageously permits for effective and safe low current stimulation.

BRIEF DESCRIPTION OF THE DRAWINGS

So that those having ordinary skill in the art to which the subject invention pertains will more readily understand how to make and use the stimulation system of the subject invention without undue experimentation, embodiments thereof will be described in detail below with respect to the figures, wherein:

FIGS. 1a-f illustrate a neurostimulator constructed in accordance with one embodiment of the subject invention, wherein the main body of the neurostimulator directly engages the cranium of a patient;

FIGS. 2a-f illustrate a neurostimulator constructed in accordance with another embodiment of the invention, wherein the main body of the neurostimulator directly engages the cranium of a patient by way of a threaded interface;

FIGS. 3a-f illustrate another embodiment of a neurostimulator constructed in accordance with the invention, wherein the main body of the neurostimulator engages the cranium of a patient by way of an intermediate mounting bracket into which the neurostimulator is snap-fitted;

FIGS. 4a-d illustrate a further embodiment of a neurostimulator constructed in accordance with the invention, wherein the main body of the neurostimulator engages the cranium of a patient by way of an intermediate mounting bracket with which the neurostimulator is threadedly engaged;

FIGS. 5a-d illustrate a neurostimulator constructed in accordance with yet another embodiment of the invention, where the neurostimulator main body is attached to the cranium by way of a strap-type mounting bracket;

FIGS. 6a-e illustrate a further embodiment of a neurostimulator constructed in accordance with the invention, which mounts to the cranium by way of tabs that project from the housing;

FIGS. 7a-e illustrate a further embodiment of a neurostimulator constructed in accordance with the invention, wherein the main body of the neurostimulator engages the cranium of a patient by way of an intermediate mounting bracket with which the neurostimulator is threadedly engaged;

FIGS. 8a-e illustrate yet another embodiment of a neurostimulator constructed in accordance with the invention, wherein the main body of the neurostimulator engages the cranium of a patient by way of an intermediate mounting bracket with which the neurostimulator is threadedly engaged, and wherein spacing shims are arranged between the mounting bracket and the neurostimulator main body;

DETAILED DESCRIPTION

Figure 2D:
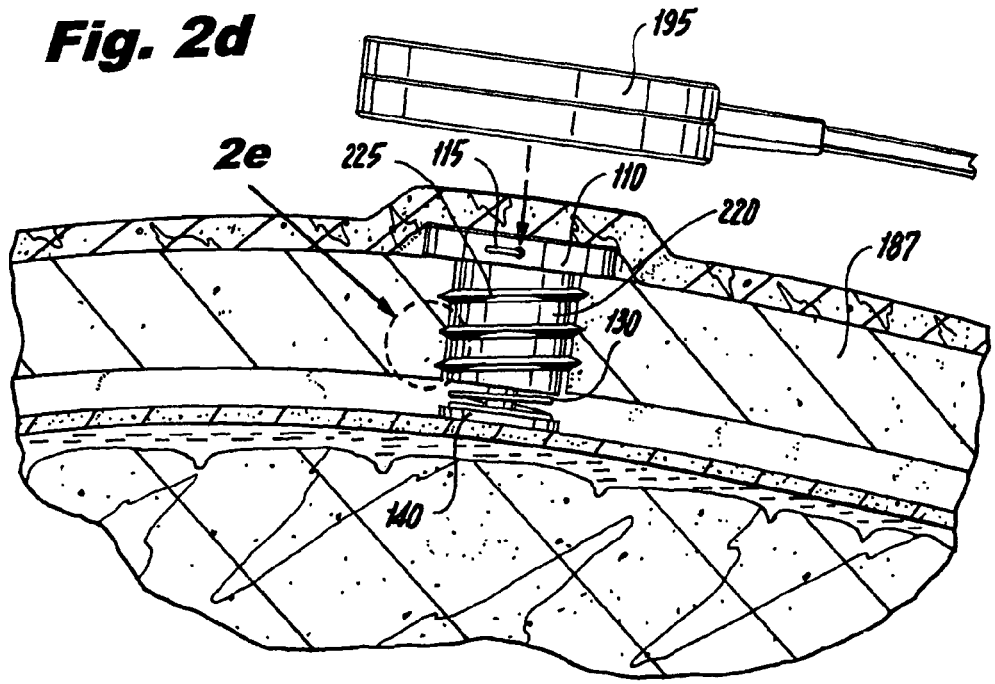

Referring now to the figures, FIGS. 1a-f illustrate a neurostimulator constructed in accordance with one embodiment of the subject invention, designated generally by reference number 100. FIG. 1a is a partial cutaway view of the neurostimulator 100 implanted in the cranium 187 of a patient. Also illustrated in these figures are the patient's brain 185, dura 181 of the brain, and cerebrospinal fluid 183 (FIG. 1f) residing therebetween.

The neurostimulator 100 includes a housing 110, and a stem 120 arranged between the housing 110 and an electrode 140 or "brain electrode". A resilient element, in this case a spring 130, is arranged between the stem 120 and the brain electrode 140. The spring biases the brain electrode 140 against the dura 181 of the brain of a patient during use, ensuring contact with the dura, but allowing the brain to move as necessary. Accordingly, a low spring constant may be used, so as to minimize resistance to movement of the brain. The length of the stem 120, by virtue of its positioning, sets a minimum distance between the housing 110 and the brain electrode 140. That is, when the spring 130 is fully compressed, a minimum distance is still maintained between the housing 110 and the brain electrode 140. An annular groove 123 is optionally provided in the distal end of the stem 120 to engage the spring 130, and prevent unintentional lateral movement of the spring, particularly when the spring 130 is compressed.

A proximal barb end 141 of the electrode 140 is received through a central aperture 127 provided in the distal end of the stem 120. It is typically preferred that either the stem 120, a portion thereof, or the barb end 141 be constructed of a material capable of elastically deforming sufficiently so as to allow entry of the barb end 141 through the aperture 127, but sufficiently stiff so that pull out of the barb end 141 from the aperture 127 is inhibited. As best seen in FIG. 1f, the barb end 141 then engages an inner distal wall 129 of the stem 120, inhibiting withdrawal therefrom. The spring 130 is thus held between the stem 120 and the brain electrode 140, and biases the electrode 140 distally with respect to the housing 110.

Neurostimulators in accordance with the invention are also provided with mounting capability for securing the neurostimulators to the cranium 187 of a patient. In the embodiment of FIGS. 1a-f, and as best seen in FIG. 1e, the neurostimulator 100 includes a close fit between the cranium 187 and stem 120. The cranium 187 and stem 120 mutually engage along the wall of the aperture 189. The engagement, in accordance with this aspect of the invention can be a compression fit, provided by a tapered aperture and matching stem shape, a friction fit due to a surface texture of the brain stem 120, a surface texture that promotes bone ingrowth, or any combination thereof.

Also, the housing 110, encloses the necessary components for effecting a therapeutic neurostimulation. Depending on the precise implementation, components housed within the housing 110 can include a receiver, a processor, memory, power storage components and/or a pulse generator, for example. The internal components can be attached to an internal or external antenna, such as external antenna 115. If provided with an external antenna, such antenna can pass through an insulated feedthrough (described in more detail in connection with the embodiment of FIGS. 6a-e).

The internal componentry is also electrically connected to the electrode through a conductive element or lead, which can be, for example, a wire 116, as shown in FIG. 1f. As with an external antenna, the wire 116 passes through an insulated feedthrough (also described in connection with the embodiment of FIGS. 6a-e) when passing through the housing 110. The internal componentry can, once set, control the treatment parameters, including mode (AC or DC), duration, polarity (anodal or cathodal), frequency and intensity of stimulation, for example, unipolar stimulation with 1 volt, at 50 Hz and a pulse width of 190 seconds.

The housing 110 may itself act as a second or "ground" electrode, completing a circuit with the first electrode 140, which contacts the dura 181 of the patient's brain 185. Accordingly, in such instances, it is particularly important in such embodiments for the conduction path from internal components to the brain electrode 140 to be insulated from the housing. In alternate embodiments, the housing 110, or parts thereof can be configured to be insulating and only have predetermined regions that function as second electrodes. Alternatively still, secondary electrodes can be carried by the housing 110, and may be arranged at any appropriate location thereon, such as at the proximal end of the neurostimulator 100, opposite the distal end, which has the brain electrode 140 arranged thereon.

The brain electrode can have any shape desired, but in the illustrated embodiments has a generally circular shape. The distal end surface of the brain electrode 140, which contacts the dura 181 is conductive in order to deliver a therapeutic electric field to effect neurostimulation in the targeted region. Optionally, the brain electrode 140, can include a plurality of discrete stimulation regions defined thereon. Such stimulation regions can be mutually divided by, for example, insulating regions disposed therebetween. Alternatively, the stimulation regions can be conductive elements disposed on an otherwise nonconductive brain electrode body. It is envisioned and well within the scope of the subject disclosure that the electrode 140 can be configured for unipolar or multipolar operation, including bipolar, quadripolar or octopolar operation, depending on the stimulation characteristic that is desired. In a unipolar or monopolar application, the housing 110 can serve as the ground or anode contact. Those skilled in the art will readily appreciate that the shape and/or configuration of the electrode 140 can vary depending upon the stimulation characteristic that is desired. For example, without limitation, the electrode 140 can be circular, annular or polygonal. It is envisioned that the electrode 140 can be configured as a paddle having one or more surface electrodes mounted thereon. Multiple electrodes can be aligned or otherwise arranged on the paddle in a manner to achieve a certain electrical field distribution pattern. It is also envisioned that two or more networked stimulators can be implanted, so that both work in conjunction to achieve a desired stimulation effect, which will be described in more detail below.

Therefore, power stored in the internal componentry within the housing 110 can be supplied through a conductive element, such as a conductive lead 116 to the brain electrode 140 and into the brain 185 of the patient. The circuit is completed through the surrounding tissue in a more diffuse manner than in the immediate area of the brain electrode 140, completing the circuit to the second electrode, which can be the housing 110 itself, depending on the precise implementation. As set forth above, particularly when provided with a resilient member, such as a spring 130, the brain electrode 140 maintains contact with the dura 181 of the brain 185, even if the brain should move slightly.

As best seen in FIG. 1d, a programmer 190 with transceiver 195 can be placed in proximity to the neurostimulator 100, to enable one-way or two-way communication with the neurostimulator. The programmer 190 can be used to initiate and control treatment, or simply to program the neurostimulator 100 for autonomous operation with the desired treatment protocol, including variable parameters such as AC or DC stimulation, duration, pulse width, amplitude, timing of treatment, frequency and polarity. Data transmitted to the neurostimulator relating to such treatment protocol is stored by the neurostimulator in memory provided in the circuitry within the housing 110, and is utilized to control operation of the neurostimulator 100 through a processor or similar element. If desired, the neurostimulator can be used to monitor neural activity in the brain of the patient, as an alternative or in addition to stimulation of the brain. Information regarding such neural activity can be stored within memory of the neurostimulator and later communicated to the programmer 190, or can be immediately transmitted to the programmer 190.

Additionally, if so desired, the programmer 190 and neurostimulator can be configured and adapted such that the programmer 190 is capable of recharging the neurostimulator 100, such as by inductive transfer of power to a charging circuit within the neurostimulator. In such an embodiment, the programmer transceiver 195 and neurostimulator 100 are each provided with a coil, the coil in the programmer inducing a current in the coil of the neurostimulator 100 to recharge one or more batteries in the neurostimulator 100.

The neurostimulator 100 is formed out of biocompatible materials such as a biocompatible polymeric material, titanium alloys, alloys of other metals and/or ceramic materials, for example. While many biocompatible materials are suitable based on biocompatibility and strength, it is also important that the materials used do not affect and are not affected by ordinary environmental factors, including exposure to magnetic fields that might be encountered in an MRI device, or x-rays that may also be used in medical imaging, for example. In a preferred embodiment, the housing 110 is formed of titanium alloy, the stem 120 is formed of a nonconductive polymeric material, and the spring 130 and brain electrode 140 are formed of titanium alloy. A conductive lead 116 is also preferably formed of titanium alloy, but can be of another conductive material.

Components that must be mutually attached, such as components forming the housing 110, can be attached with any suitable method, such as adhesives including epoxies, welding and the like. In a preferred embodiment, attached components are laser welded to one another.

If bone ingrowth into a component of the neurostimulator 100 is desired to help anchor the neurostimulator in place, such as into the stem 120, the stem 120 can be formed of a porous ceramic material, a sintered metal material and/or a material having a hydroxyl apatite coating, for example. Also, although shown with a square incision in FIG. 1b, for example, it is to be understood that differently shaped incisions are applicable, including linear incisions.

Neurostimulators in accordance with the invention can be any size necessary, although in general are not very large. In accordance with one embodiment of the invention, the housing 110 is about 25 mm in diameter, while the stem 120 is about 10.5 mm in diameter, with the overall height of the neurostimulator being about 18.5 mm.

Figure 2E:
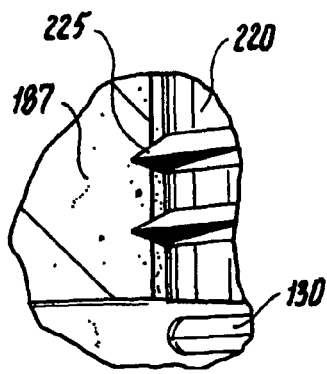
Figure 2F:
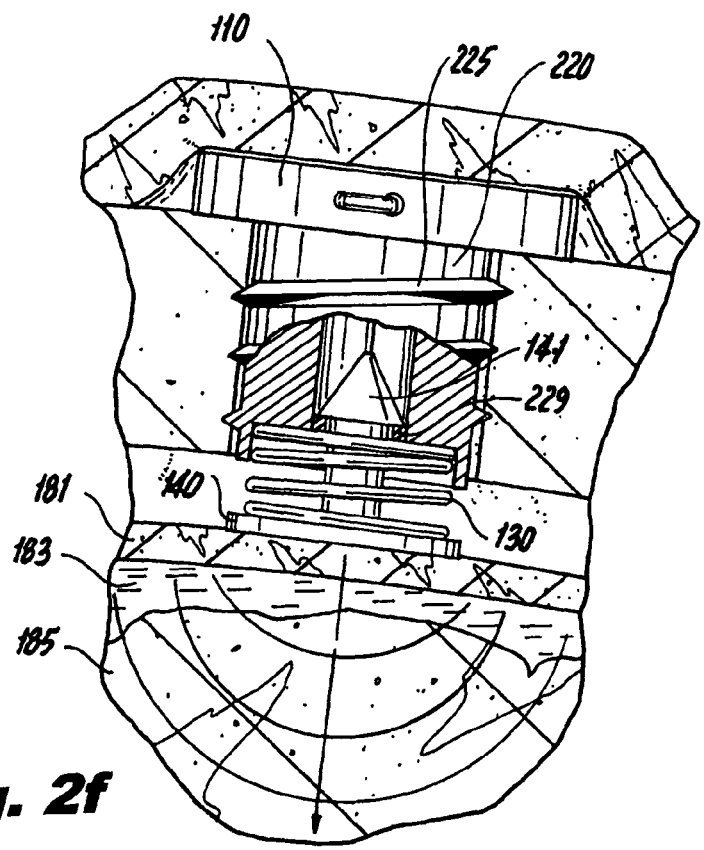

FIGS. 2a-f illustrate a further embodiment of a neurostimulator 200 constructed in accordance with the invention. The neurostimulator is similar in many respects to the neurostimulator 100 of FIGS. 1a-f, and therefore, like reference numbers have been used to refer to like elements. The neurostimulator 200 of FIGS. 2a-f differs from the embodiment of FIGS. 1a-f primarily in the connection between the neurostimulator 200 and the cranium 187 of the patient. The neurostimulator 200 includes a stem 220 having threads 225 formed on the outer surface thereof. As best seen in FIGS. 2d-f, the threads 225 engage the cranium 187, inhibiting direct pullout of the neurostimulator 200. The threads 225 can be adapted and configured to "self-tap" the cranium 187, or can be inserted into the cranium 187 following a tapping step, whereby a helical groove is cut into the edge of the aperture 189 formed in the cranium 187.

Insertion of the neurostimulator 200 into the aperture 189 is effected by way of screwing the neurostimulator into the aperture 189. As the neurostimulator 200 advances through the aperture, the brain electrode 140 will eventually come into contact with the dura 181. Advancement may be stopped any point desired, or the neurostimulator 200 can be advanced fully into the aperture 189 to a point where the housing 110 abuts the upper surface of the cranium 187, for example.

The stem 220 includes at its distal end, a recess 224 in which the resilient member—again, a spring 130—partially resides. This recess 224 serves the purpose of the annular groove 123 of the neurostimulator 100 of FIGS. 1a-f by stabilizing the spring 130, preventing the spring from dislodging from the stem 220. Naturally, a groove, such as groove 123 can be applied to this embodiment as well. The brain electrode 140 is inserted through the aperture 227 formed in the stem 220, with its barb end 141 engaging the distal internal wall 229 of the stem 220 and compressing the spring 130.

FIGS. 3a-f illustrate various views of another embodiment of a neurostimulator 300 constructed in accordance with the invention. Where the foregoing embodiments are configured to directly engage a wall of an aperture 189 formed in the cranium 187 of a patient, the neurostimulator 300 of FIGS. 3a-f is provided with a mount 350, which is first inserted into the aperture 189, before the remainder of the neurostimulator 300. The mount 350, as embodied, includes an annular body 355 and an attached flange 353 with screw holes 352 formed therein. Screws 351 are used to attach the mount 350 to the cranium 187.

Figure 3D:
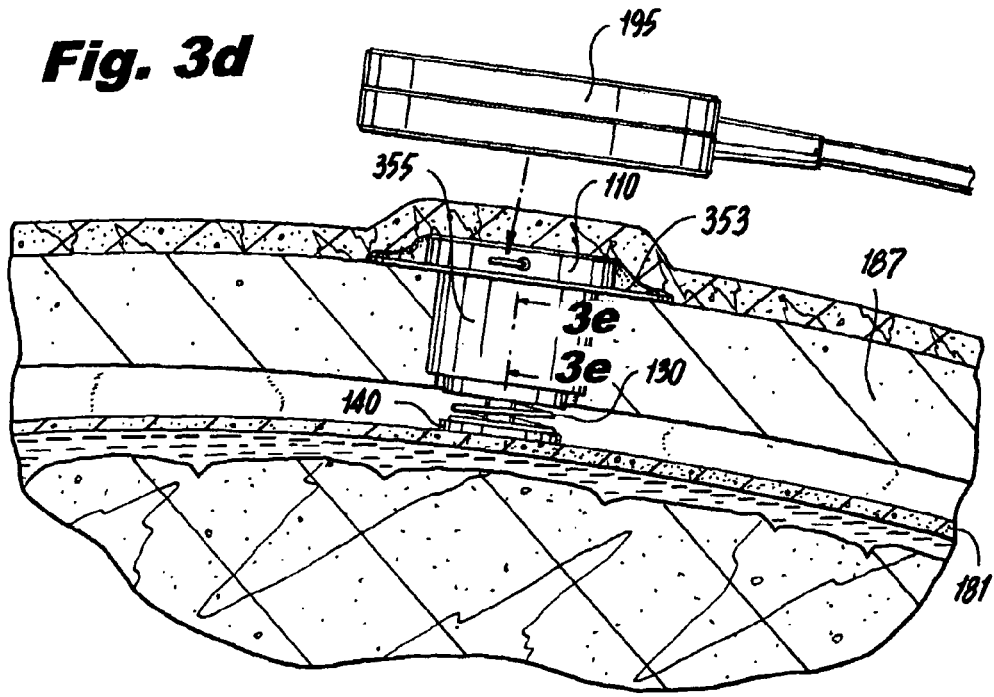
Figure 3E:
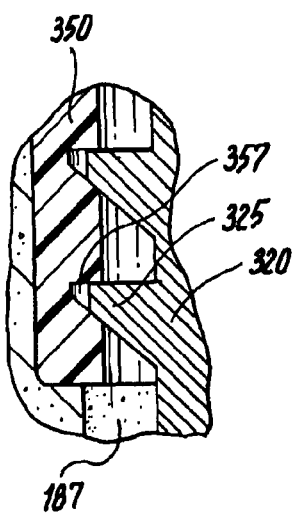
Figure 3F:
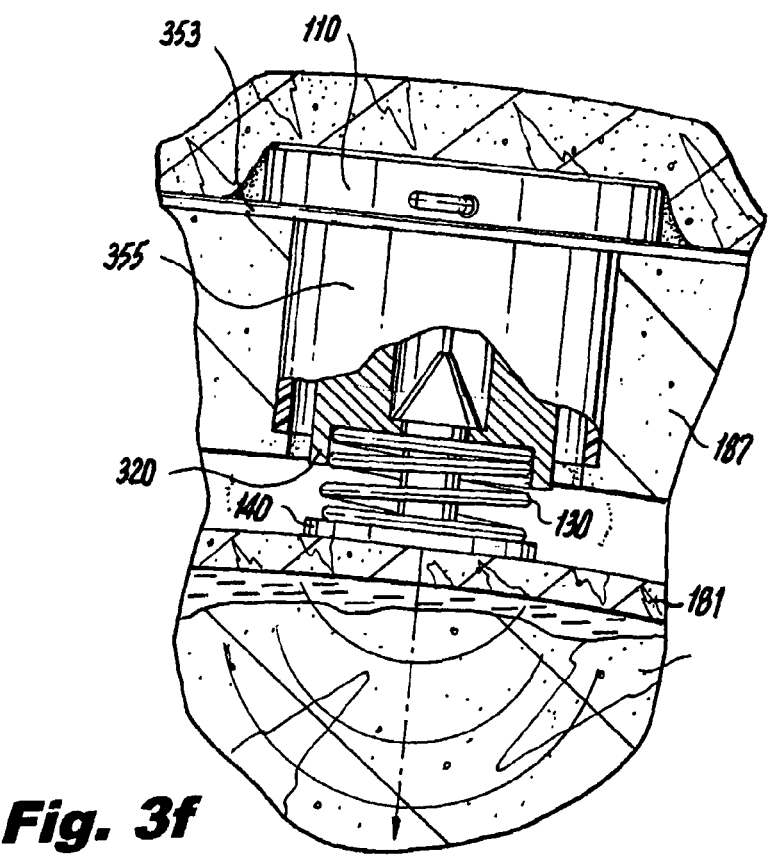

The main body portion 301 of the neurostimulator 300, which includes the housing 110, stem 320, spring 130 and electrode 140, are then inserted into the mount 350. In the embodiment illustrated in FIGS. 3a-f, and as best seen in FIGS. 3b, 3c and 3e, annular barbs 325 are arranged on the outer surface of the stem 320, and engage mating annular recesses 357 in the mount 350. The distal face of each annular barb 325 is angled, and the proximal face is perpendicular with respect to the longitudinal axis of the neurostimulator 300 in order to facilitate insertion into while inhibiting removal of the main body portion 301 from the mount 350.

Although illustrated in FIGS. 3a-f with equal numbers of annular barbs 325 and annular recesses 357, specifically, two of each, this need not be the case. The neurostimulator 300 can be configured so that the increments between annular barbs and recesses, or similar mutually engaging elements provides a range of insertion increments which can allow the surgeon to advance the main body portion 301 of the neurostimulator 300 in the mount 350 incrementally until the desired contact, as gauged by pressure or electrical conductivity with the brain, for example, is reached. Such increments can be relatively large, as illustrated, or can be much smaller, such as at 0.5 mm increments, for example.

Naturally, the precise configuration of the engagement need not be as illustrated. Other configurations that enable a snap-fit of the main body portion 301 into the mount can be applied to the present embodiment or other embodiments set forth herein. An alternate attachment to a mount is illustrated in the embodiment of FIGS. 4a-d. Alternatively, other types of mutual engagement are applicable to this aspect of the present invention, including a bayonet-type locking feature, for example.

Moreover, the mount 350 is illustrated with a flange 353 that mounts to the outer surface of the cranium 187, which results in the housing 100 extending a small distance about the surface of the cranium 187. Although the distance that the housing 100 extends above the cranium 187 is not large, the mount 350 can be adapted so that the housing 110 is partially or fully recessed below the outer surface of the cranium 187. Naturally, the diameter of the housing 100 can be relatively smaller, so that the entire main body portion 301 can fit within the mount 350. These optional features may also advantageously be applied to other embodiments of neuro stimulators described herein.

FIGS. 4a-d illustrate a further embodiment of a neurostimulator 400 in accordance with the invention. Elements that are identical to foregoing embodiments are indicated by the same reference number, and analogous elements are indicated by similar reference numbers. As with the embodiment of FIGS. 3a-f, the neurostimulator includes a mount 450 into which a main body portion 401 is inserted. In this embodiment, the stem 420 includes helical threads on the outer surface thereof to engage a matching helical groove 457 in the mount 450. The mount 450 includes a mounting flange as with the embodiment of FIGS. 3a-f, which is first attached to the cranium 187. Of course, if desired, the main body portion 401 of the neurostimulator can be attached to the mount 450, and then attached to the cranium by screws 351. As with any embodiment set forth herein, the stem 420 can be provided with a groove 123 as illustrated in FIG. 1c for retaining the spring 130, or can be provided simply with a recess 224, as in FIG. 2c.

Advantageously, the nature of the interface between the main body portion 401, having helical threads 425 on the stem 420 thereof, and the mount 450, having a mating helical groove 457, allows the surgeon to adjust the relative position between the mount 450 and the main body portion 401, and thus also between the brain and the electrode 140. Such adjustment may be desirable during installation of the neurostimulator, in order to ensure proper contact between the electrode 140 and the patient's brain, for example.

With respect to other aspects of the neurostimulator, including the housing 110, components held therein, the spring 130 and electrode 140, for example, such features can be as described in connection with other embodiments set forth herein. In general, any feature described in connection with one embodiment of the invention can be applied to another embodiment of the invention.

FIGS. 5a-d illustrate various embodiments of neurostimulators constructed in accordance with the invention, which are secured to the cranium 187 of the patient by way of a bracket secured over the neurostimulator 500, and to the cranium 187. In the embodiment of FIGS. 5a-d, the neurostimulator 500 itself is essentially the same as, and includes the same basic set of components as the neurostimulator 100 of FIGS. 1a-f. The neurostimulator 500 can include any of the attachment features described in connection with the neurostimulator 100 of FIGS. 1a-f, or can be configured to simply fit within the aperture 189 formed in the cranium 187 of the patient without any direct attachment between the neurostimulator 500 and the cranium 187. Instead, a bracket is provided which engages the neurostimulator 500, and which is directly secured to the patient's cranium 187, thereby securing the neurostimulator 500 to the cranium 187.

Figures 5A, 5B:
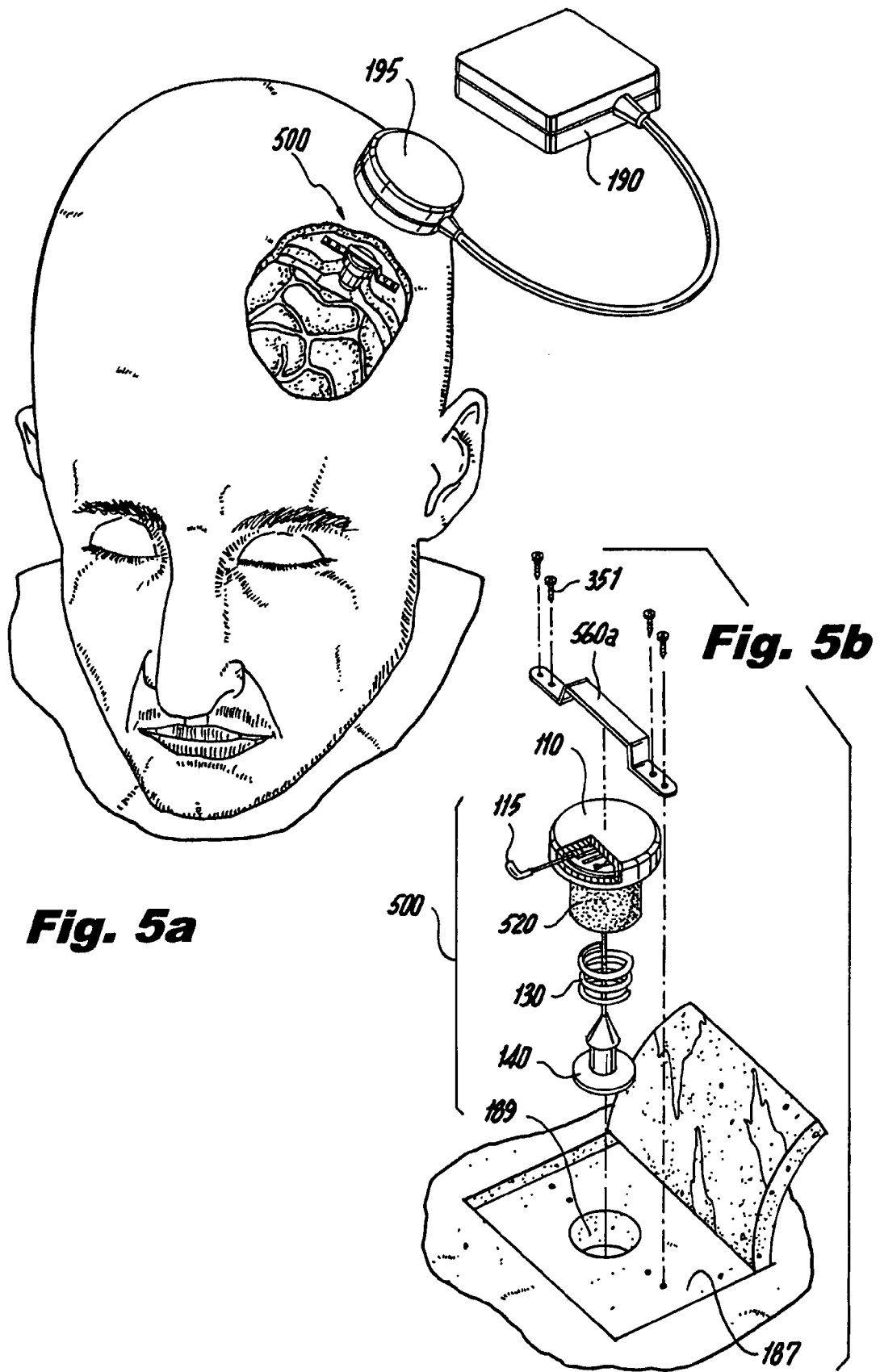

In the embodiment of FIGS. 5a-b, the bracket 560a is substantially linear in plan view, and includes symmetrical bends, which form a crook that engages the housing 110. Screw holes are provided in the ends of the bracket 560a, to allow passage of screws 351 through the bracket 560a, and into the cranium 187, thereby securing the bracket 560a and the neurostimulator to the cranium 187.

The embodiment of FIG. 5c illustrates the neurostimulator 500, which itself is the same as that illustrated in FIGS. 5a-b, and a generally X-shaped bracket 560b for securing the neurostimulator 500 to the cranium 187 of the patient. As embodied, the bracket 560b is contoured so as to engage the housing 110 when placed over the housing. Mechanical attachment means for attaching the bracket 560b to the cranium 187 of the patient are provided—particularly, screw holes placed at the ends of the bracket for use with screws 351. Further, if desired, a seal 581 can be provided between the cranium 187 and the neurostimulator 500 to compensate for any irregularities therebetween. The seal 581 can be applied directly to the cranium 187, directly to the neurostimulator 500, or can be in the form of an O-ring, for example, that is placed between the cranium 187 and the neurostimulator 500. Naturally, this feature can be applied to any embodiment set forth herein.

The embodiment of FIG. 5d illustrates still another embodiment of the neurostimulator and a securing bracket 560c. In this embodiment, the bracket 560c includes an enlarged cap portion 567 and two diametrically opposed tab portions 569, for securing the cap 560c and the neurostimulator 500 to the cranium of the patient 187, by way of screws, for example. The cap 560c can be provided with a circumferential lip 565, as illustrated, to aid engagement with the neurostimulator 500.

Figure 6A:
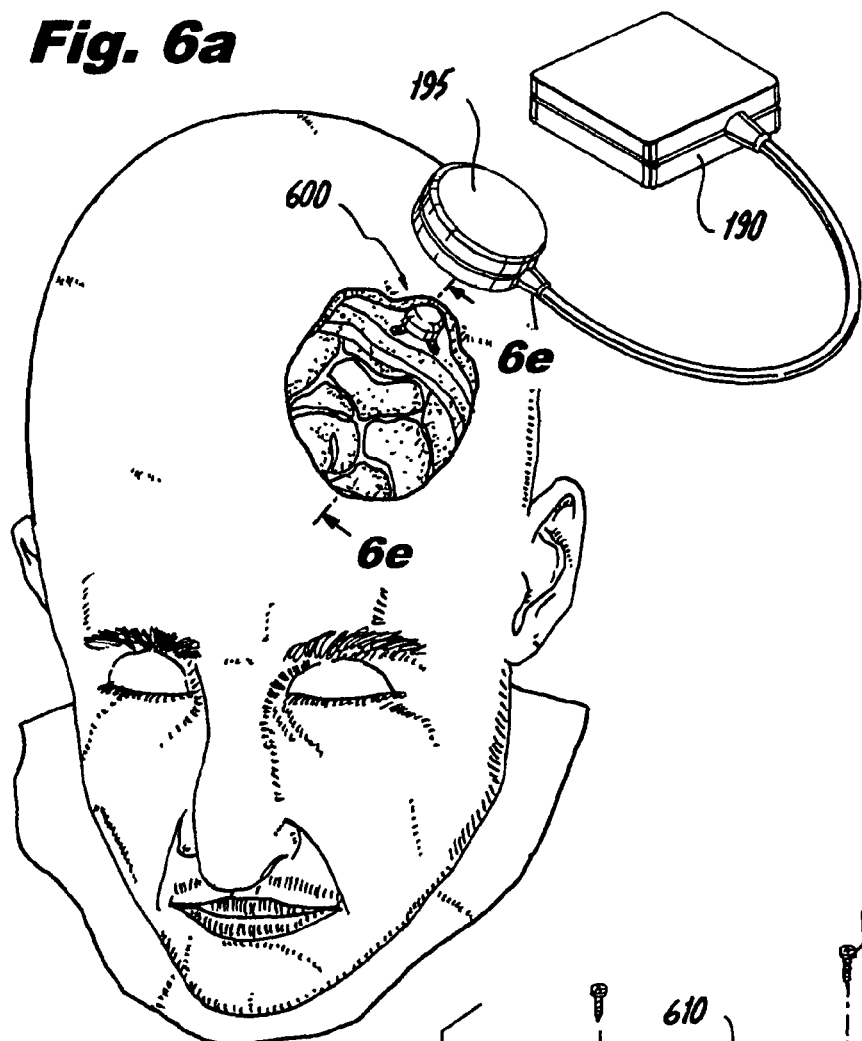
Figure 6B:
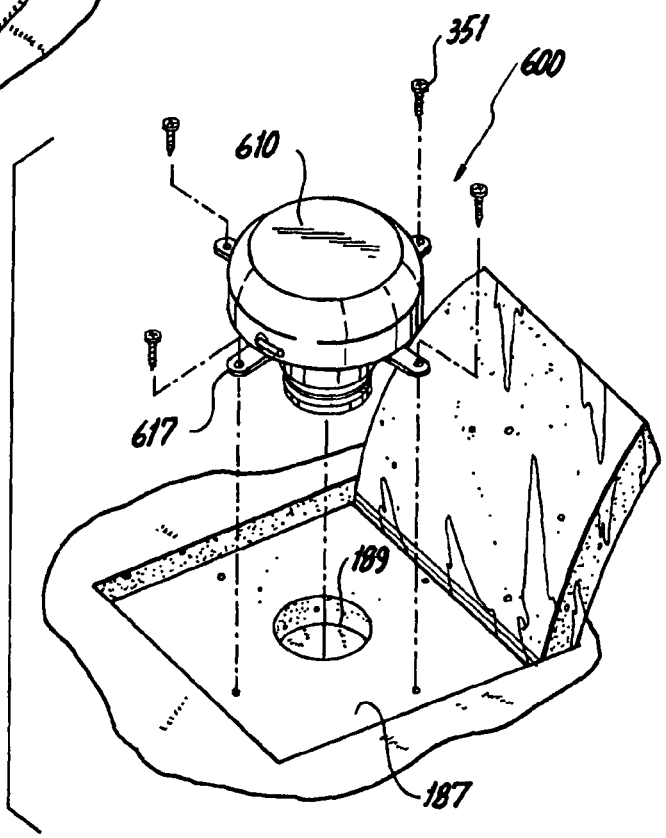

FIGS. 6a-6e illustrate a further embodiment of a neurostimulator 600 in accordance with the invention. As seen in FIGS. 6a and 6b, the neurostimulator 600 is attached to the cranium 187 with screws 351, which are inserted through radial tabs 617 extending from the housing 610 of the neurostimulator 600.

FIGS. 6c-6d are exploded views of the neurostimulator 600, illustrating individual components thereof and their relative orientation with respect to one another. The housing 610 includes both a cap portion 610a and a floor portion 610b. The cap portion 610a is arranged at the proximalmost end of the neurostimulator 600 and includes an aperture 613, which permits an insulated pass-through 614 for the antenna 115 to pass through the housing 610, if so-embodied. Alternatively, the antenna may be fully contained internally to the housing. In either case, the antenna 115 is connected to internal componentry 619 of the neurostimulator 600. A floor portion 610b of the housing 610 is sealed to the cap portion 610a, securing within the housing 610, the internal componentry 619. The floor 610b can be sealed with a polymeric adhesive or sealant, or in a preferred embodiment, laser welded thereto. A second insulated pass-through 624 is provided in the floor 610b, which allows a therapeutic electrical impulse to reach the electrode 140 by way of a conductor 680 connected therebetween, through the floor 610b.

A retainer ring 611 is secured to the floor 610b, and facilitates engagement between the housing 610 and the stem 620. The retainer ring 611 is preferably made of the same material as the housing and attached thereto by laser welding, or integrally formed therewith. Alternatively, the retainer ring 611 can be made of any suitable material of sufficient strength and durability. Moreover, the retainer ring 611 can be provided with a stepped undercut 612 (FIG. 6d) to facilitate a snap-fit engagement with the proximal end of the stem 620, where the stem 620 is provided with a mating engagement feature, such as undercut 622. The retainer ring 611 can also be formed so as to include a split 616, which can have a corresponding protrusion 621 arranged on the stem 620. Together, the split 616 and the protrusion 621 inhibit relative rotation between the stem 620 and the retainer ring 611.

The stem 620, as set forth above, can be configured to engage with the housing, particularly the retainer ring 611, by snap fit. Such snap fit is preferably sufficiently robust enough that no other mechanical connection between the stem 620 and housing 610 is required. However, if desired, adhesive can be alternatively or additionally used to connect the stem 620 and the housing 610. Naturally, other mechanical connections can be used in place of that described above without departing from the scope of the invention. As with the embodiment of FIGS. 1a-f, a groove 623 can be provided on the distal end of the stem 620 for engaging the spring 130. The aperture 627 provided in the stem 620 receives the proximal end of the electrode 140, as described in connection with the embodiment of FIGS. 1a-f, thereby holding the spring in place therebetween.

Figure 7A:
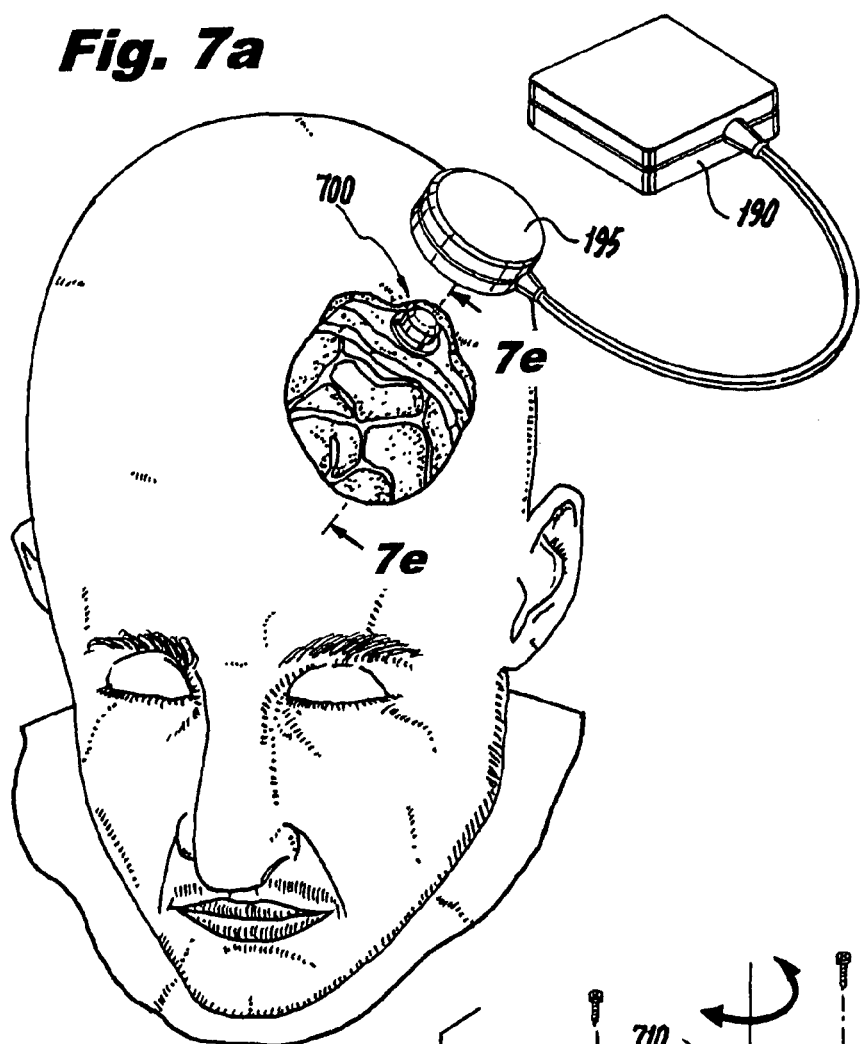
Figure 7B:
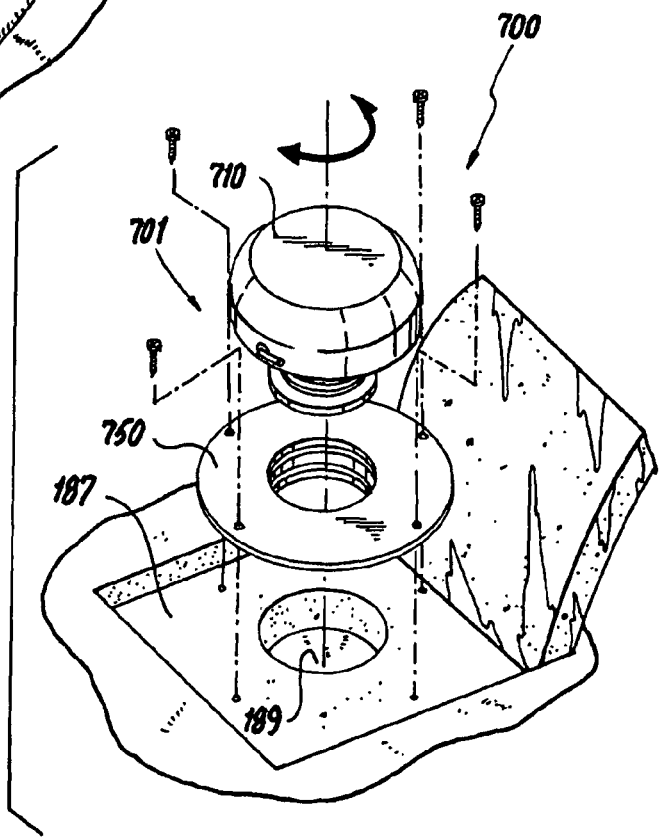
Figure 8A:
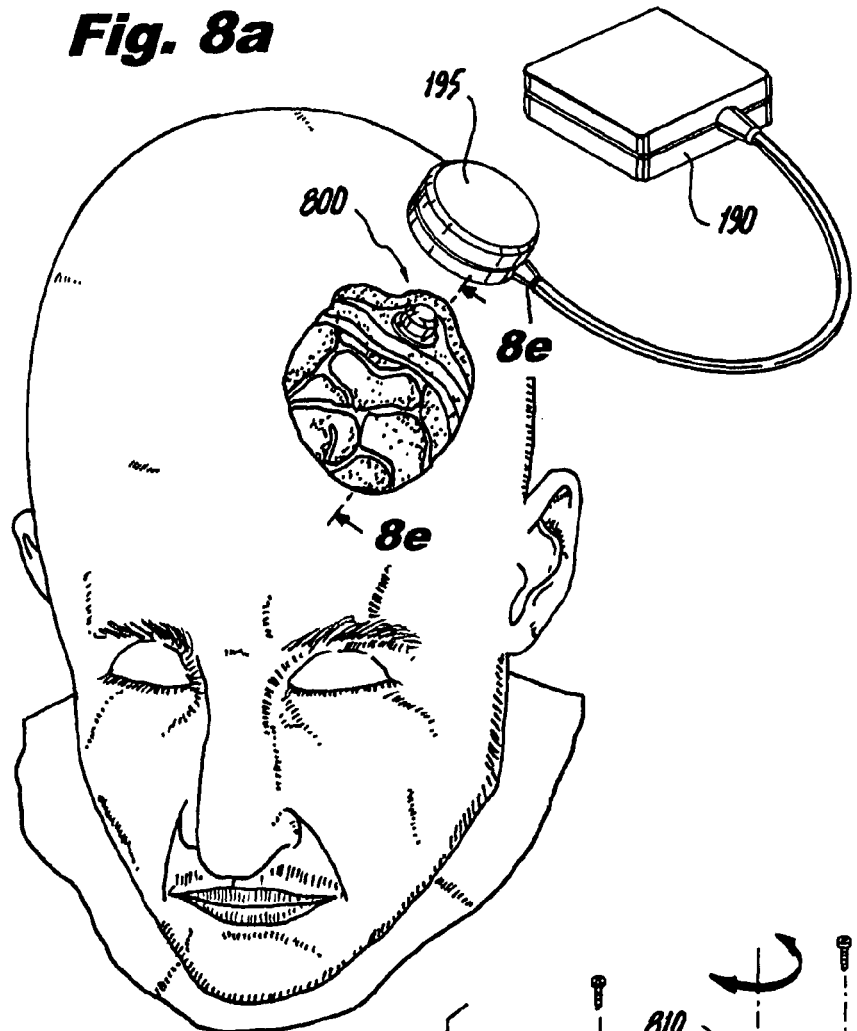
Figure 8B:
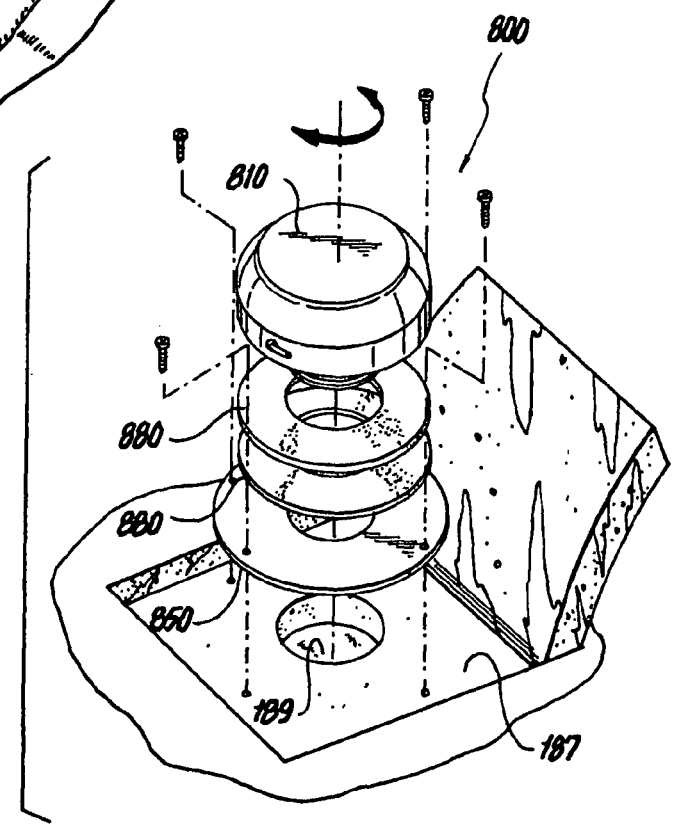

FIGS. 7a-e illustrate a further embodiment of a neurostimulator 700 constructed in accordance with the invention. The neurostimulator includes a mount 750 into which a main body portion 701 is inserted. In this embodiment, the stem 720 includes helical threads 721 on the outer surface thereof to engage matching helical threads 751 in the mount 750. The mount 750 includes a mounting flange as with foregoing embodiments. In use, the mount 750 is first attached to the cranium 187, with the main body portion 701 being inserted thereafter. Of course, if desired, the main body portion 701 of the neurostimulator can be attached to the mount 750, and subsequently attached to the cranium by screws or other suitable attachment means. As with any embodiment set forth herein, the stem 720 can be provided with a groove 123 as illustrated in FIG. 7c for retaining the spring 130. Alternatively, the stem 720 can simply be provided with a recess as shown by recess 224, of FIG. 2c. Advantageously, the threaded interface between the stem 720 and mount 750 allows for adjustability, if adjustability is desired or required.

The retainer lip 711 provided in the embodiment of FIGS. 7a-7e includes a discontinuity 716, as best illustrated in FIGS. 7c and 7d. This allows for locking engagement with the stem 720. The discontinuity 716 in the retainer lip 711 allows, more specifically, for engagement with locking anti-rotation protrusion 726 provided on the stem 720. The retainer lip 711 and the mutually engaging part of the stem 720 can be shaped to as to allow for a press-fit, snap-fit or other secure mutual engagement arrangement. If so desired, the mutual engagement of the retainer lip 711 and stem 720 can be permanent or reversible, depending on the precise implementation.

Additionally illustrated is an electrical a conductor 780, which leads from the feedthrough 624 provided in the lower wall 618 of the housing 710, to the electrode 140. Accordingly, a therapeutic electrical stimulus can be delivered through the electrode to the patient's brain.

Moreover, as with other embodiments described herein, the housing 710 can include additional components held therein. In general, any feature described in connection with another embodiment of the invention can be applied to the embodiment illustrated in FIGS. 7a-7e.

FIGS. 8a-e illustrate a further embodiment of a neurostimulator 800 designed and constructed in accordance with the invention. As with some or all of the foregoing embodiments, the neurostimulator 800 is provided with a housing 810 having a bottom wall 818, a mount 850 for mounting to the cranium 187, internal componentry 619, a stem 820, and other elements. What is notably different between the neurostimulator 800 of FIGS. 8a-8e is the absence of a resilient biasing member such as a spring. Instead, spacing between the electrode 140 and brain is determined and maintained by shims 880 which reside between the housing bottom wall 818 and the mount 850. The housing 810 is connected through its bottom wall 818, retainer lip 711 to the stem 820. The electrode 140 also engages the stem 820, which in-turn engages the mount 850. Although threads 821 are illustrated, other engagements are conceived to allow relative mutual engagement such as a bayonet-type key-and groove of press-fit, for example. Such mutual engagement, in cooperation with the shims 880, maintains the relative spacing between the electrode 140 and the patient's brain.

Further in accordance with the invention, neurostimulators are provided which are adapted and configured to be networked to operate jointly in order to effect a therapeutic result. Under normal circumstances, a healthy, uninjured brain utilizes multiple regions simultaneously to conduct unique function. For example, speech requires coordination between different areas of the brain, including Broca's area, Wernicke's area and a supplementary motor area. Following injury resulting in brain damage, such as stroke, functional reorganization of the surviving portions of the brain occurs to compensate for lost function. Regions surrounding those previously engaged in the same function are conscripted for reorganization. Such areas are usually larger than the areas that formerly performed that function Applicant recognizes that neurostimulation can enhance the recovery process, and if multiple areas are necessary for recovery, that it is beneficial to co-stimulate such areas, which can include excitation or inhibition, depending on the status of that region of the brain.

Networking of a plurality of discrete neurostimulators, as described hereinabove, can achieve the aforementioned result. If actuated simultaneously, such a plurality of neurostimulators can yield an electrical field of increased size that is capable of stimulating a larger area than a single, discrete neurostimulator alone. Such stimulation can enhance cortical plasticity and therefore can enhance recovery. Through the use of electronic controls, different electrodes of the neurostimulator(s) can be activated at different times and with different therapeutic parameters, including different mode (anodal or cathodal) voltage, duration and interval between successive impulses.

Alternating current (AC) or direct current (DC) can be used as required or desired to achieve the desired stimulation. For instance, in cases such as epilepsy or Parkinson's disease, in which brain excitability increases, high frequency AC stimulation or cathodal DC stimulation is effective in reducing the excitability. On the other hand, as in cases of stroke, where brain excitability decreases, facilitatory AC stimulation or anodal DC stimulation is effective. Moreover, individual neurostimulators in accordance with the invention may be equipped with multiple electrodes. Such multiple electrodes can be adapted to have the same polarity and act as in unison as a single pole, with a relatively remotely oriented opposite pole, such as the housing of the neurostimulator, as described above. Alternatively, the multiple electrodes can be adapted to have opposite polarity to one another in order to effect simulation in the areas immediately surrounding the electrodes. For example, in stroke patients, ipsilateral premotor area requires facilitatory stimulation; whereas the contralateral motor area may require inhibitory stimulation.

Figures 9A, 9B:
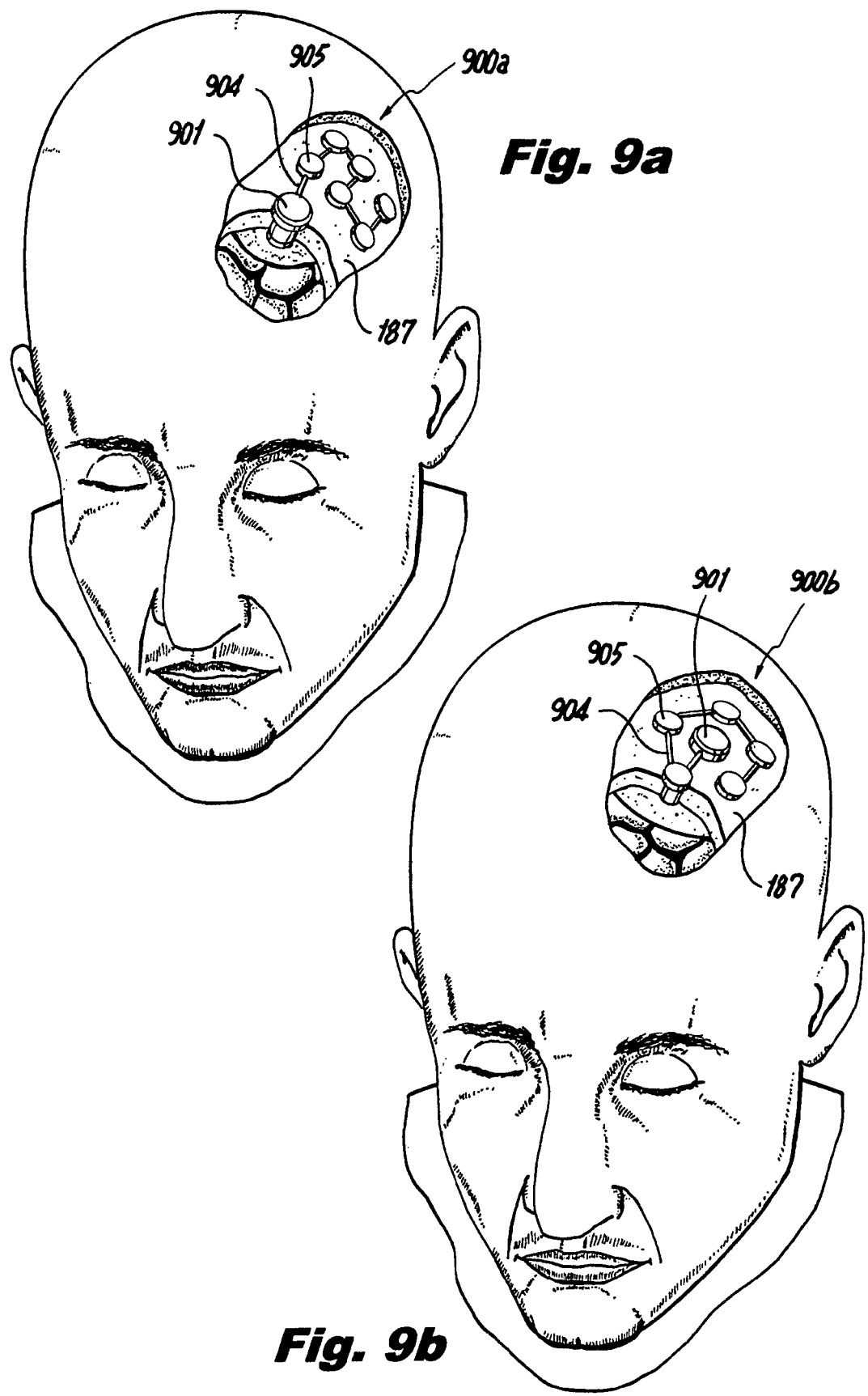
FIGS. 9a-c illustrate embodiments of networked neurostimulator systems arranged in respective arrays in accordance with the invention (One or more electrodes can be used in combination with or in place of one or more secondary neurostimulators in this or other embodiments set forth herein)
Figure 9C:
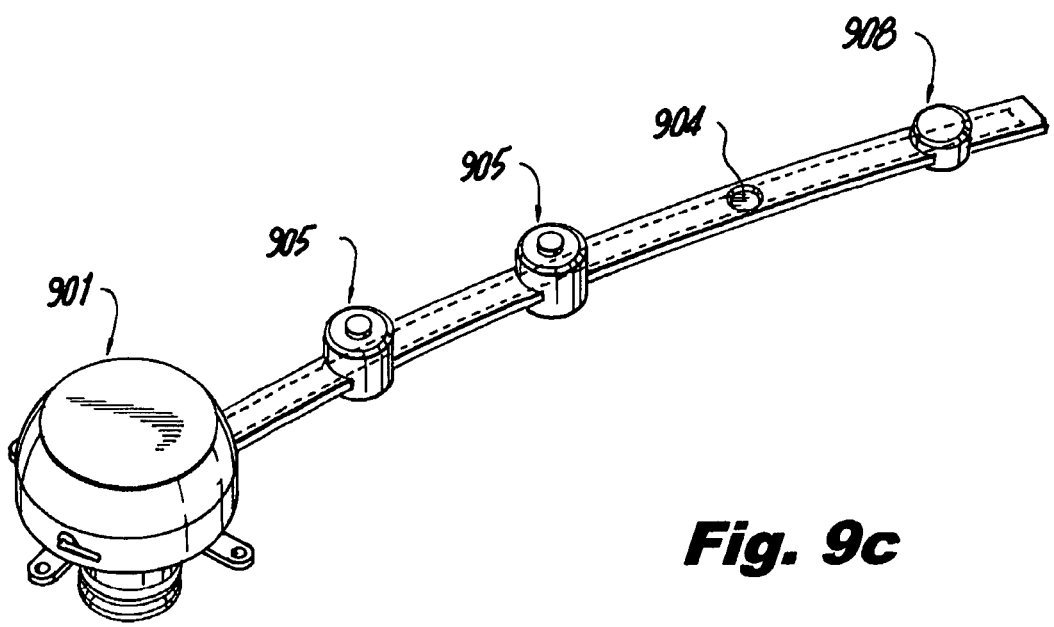

FIGS. 9a-9c illustrate embodiments of neurostimulator systems arranged in respective arrays 900a, 900b, in accordance with the invention. The array of FIG. 9a is a rectangular array, while the array of FIG. 9b is substantially circular in shape. As illustrated, a controlling neurostimulator 901 is provided in combination with companion neurostimulators 905, which alternatively can be embodied simply as electrodes. For simplicity, such alternatives may not be pointed out in each instance throughout this document, but it is to be understood that such a substitution can be made, and in some cases may be preferable. The controlling neurostimulator 901 and companion neurostimulators 905 are networked so as to synchronize therapeutic treatment across various regions of the brain.

The networking can be effected wirelessly or with a physical conductive lead 904. The systems can be configured so that the conductor 904 carries data, such as may be received from a programmer 190. Additionally or alternatively, power may be transmitted through the conductor 904 to drive each companion neurostimulator 905. The power supplied can go through internal componentry in the companion neurostimulator 905, or alternatively, the power can be a therapeutic electrical impulse that is merely passed through the companion neurostimulator 905 to the patient's brain. Accordingly, the companion neurostimulators 905 can be physically configured in the same manner as those neurostimulators described herein in connection with the foregoing embodiments, or alternatively, the companion neurostimulators 905 can be simpler in construction. Naturally, if electrodes lacking the capability to independently generate a therapeutic impulse are used, another pulse generator, such as one housed within a controlling neurostimulator is used, with the power being transmitted by way of a conductive lead.

Alternatively still, the companion neurostimulators can receive a control signal from the controlling neurostimulator 901, which triggers the companion neurostimulator(s) to release a therapeutic electrical impulse.

Further, the companion neurostimulators 905 can be essentially autonomous, being addressed only initially or periodically to set treatment protocol.

FIG. 9c schematically illustrates an arrangement for connection of the controlling neurostimulator 901 and the companion neurostimulators 905 by way of the conductor 904. The conductor 904 is preferably well insulated, for example by a sheath of silicone rubber. The neurostimulators 901, 905 can be adapted to automatically puncture the sheath when applied thereto. Moreover, if an error is made in placement, a repair covering 908 can be applied over the conductor to prevent an errant electrical discharge.

Figure 10:
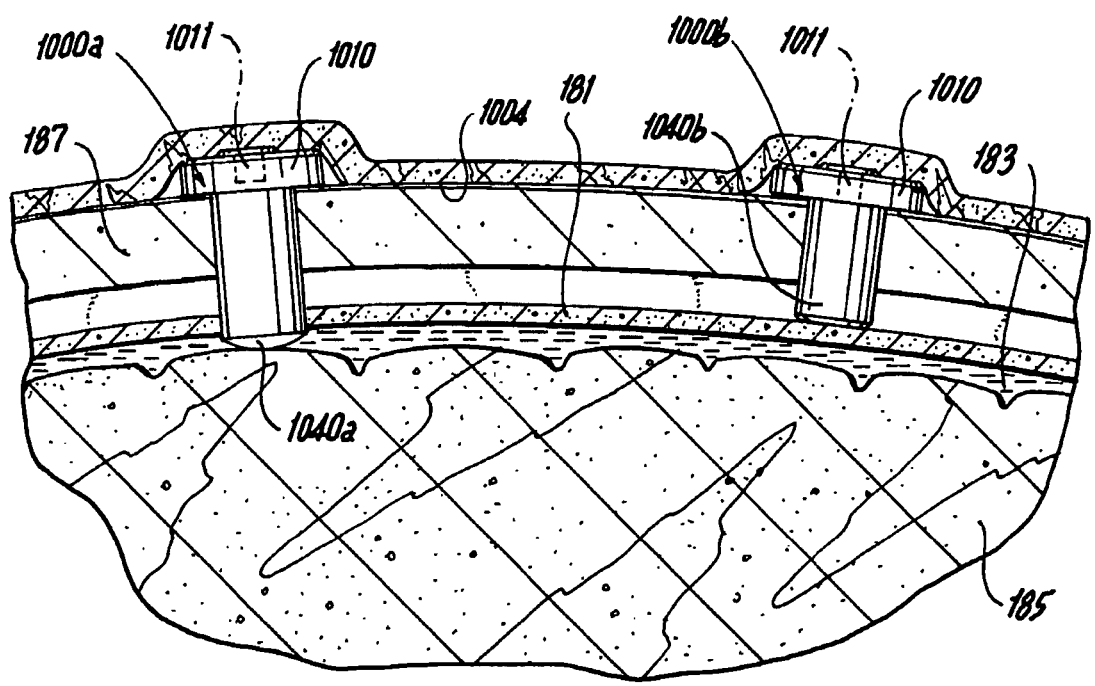
FIG. 10 illustrates networked neurostimulator(s) and/or electrodes in accordance with the invention, wherein intradural-type and extradural-type electrodes are used jointly in the same network.

FIG. 10 is a partial view of an embodiment in accordance with the present invention including networked neurostimulators, including an extradural-type neurostimulator 1000b, such as those described above, used in combination with an intradural-type neurostimulator 1000a. The intradural neurostimulator 1000a is particularly useful in cases of brain atrophy, where the brain electrode, such as brain electrode 1040b, would not rest close enough to the brain cortex to result in an electrical field adequate to evoke a therapeutic response. The electrode 1040b of the extradural neurostimulator 1000b terminates external with the dura 181. However, if the brain cortex has atrophied due to a stroke or for other reasons, the electrode 1040b may not rest near enough to the cortex to be effected by the electrical field transmitted through the electrode 1040b.

However, the intradural neurostimulator 1000a is adapted and configured to extend through the dura 181 of the brain 185, and therefore terminates more closely to the brain cortex in atrophied regions. The electrode 1040a of the intradural neurostimulator 1000a can be adapted and configured to include a relatively spheroidal shape, as illustrated in order to better distribute a therapeutic electrical field to the surrounding neural tissue, and to prevent damage to the surrounding cortical surface.

Figure 12A:
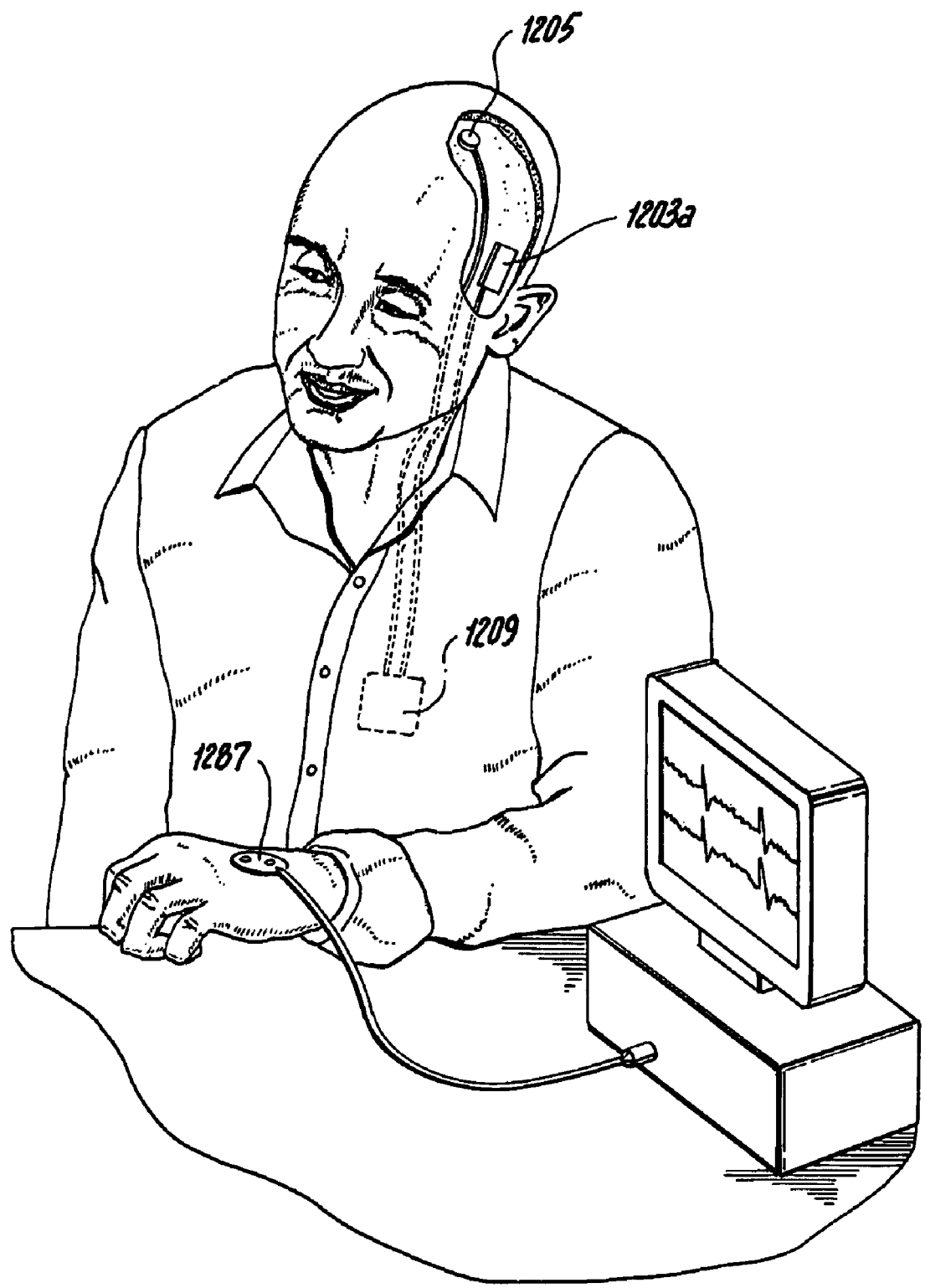
FIG. 12a illustrates networked neurostimulators and/or electrodes, which may include separate electrodes, in accordance with the invention, arranged on a patient's brain, and prepared for use in calibrating a treatment protocol by measuring brain excitability by way of induced motor evoked potential.

As with foregoing embodiments, a conductor in the form of a conductive lead 1004 can be used to interconnect all neurostimulators, electrodes, and/or separate implantable control units or pulse generators, if so-embodied (see FIG. 12a, for example). Electrical connections between the neurostimulator(s) and/or electrode(s) and any conductor(s) can include a through connection, in which the conductor 1004 continues from one neurostimulator or electrode to the next, and electrically contacts a conductive component within the neurostimulator or electrode in order to transmit a control signal and/or to provide power to the neurostimulator or electrode. The electrical connection may include a piercing element that pierces the insulation of the conductor 1004. Such piercing elements can be activated by advancing a screw or by closing the housing of the neurostimulator over the conductor 1004, for example. However, other connection arrangements can be utilized in accordance with the invention. Alternatively or additionally, communication between neurostimulators and/or a controller can be effected wirelessly, as described hereinabove.

Figure 11A:
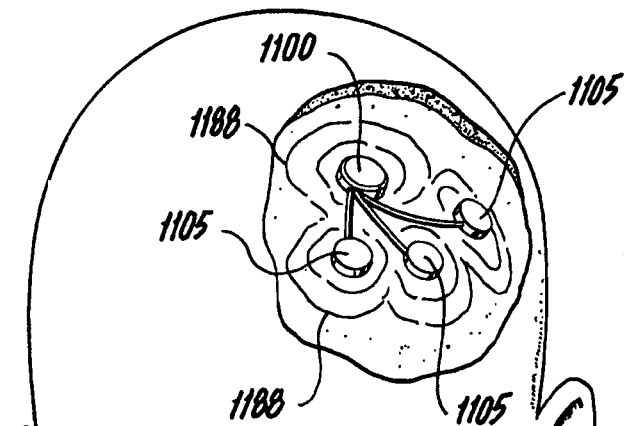
FIG. 11a illustrates networked neurostimulators in accordance with the invention, wherein satellite neurostimulators and/or electrodes are physically arranged in parallel to a controlling neurostimulator.

FIG. 11a illustrates networked neurostimulators and/or electrodes physically connected in parallel and arranged with respect to the brain, for premotor, motor cortex, and supplementary motor area stimulation, as an example. Such arrangements can be embodied such that all neurostimulators or electrodes are controlled simultaneously on one control channel, or alternatively, so that the neurostimulators or electrodes are controlled in one or more groups, on one or more respective control channels. Accordingly, the controlling neurostimulator 1100 and the companion neurostimulators 1105, can be actuated independently with individual treatment protocol. As illustrated, a controlling neurostimulator 1100 is connected to three companion neurostimulators 1105 and/or to simple electrodes. Such companion neurostimulators can receive power, control signals, or both power and control signals from the controlling neurostimulator 1100. Again, if electrodes lacking the capability to independently generate a therapeutic impulse are used, another pulse generator, such as one housed within the controlling neurostimulator 1100 is used, with the power being transmitted by way of a conductive lead.

Typically, it is necessary that the controlling neurostimulator 1100 be somewhat larger than the companion neurostimulators 1105, in order to house the necessary power supply and/or electronic components. Advantageously, companion neurostimulators can be low profile for cosmetic or other purposes. That is, the housing of the companion neurostimulators do not necessarily include circuitry of the controlling stimulator, and can therefore be significantly smaller than that of the controlling neurostimulator. Thus, a patient with multiple neurostimulators need not have multiple noticeable bumps under his or her scalp, although typically, even the controlling neurostimulators are relatively low-profile in accordance with the invention.

Accordingly, companion neurostimulators can be similar in configuration and attachment as those set forth above, for example in connection with FIGS. 1-8. However, as set forth above, conventional electrodes can also be used in place of such companion neurostimulators. Alternatively, any or all of the networked neurostimulators can have different physical designs, not specifically set forth herein, but which function in accordance with the invention.

The embodiment of FIG. 11a, as illustrated, includes representative electric field lines 1188, representing field lines due to independent, non-simultaneous activation of the controlling neurostimulator 1100 and companion neurostimulators 1105 and/or electrodes. This arrangement is useful for stimulation (activation or inhibition) of multiple functional regions at different times. Such stimulation can be contrasted with the effect of simultaneous stimulation, which is represented in the embodiment of FIG. 11b.

Figure 11B:
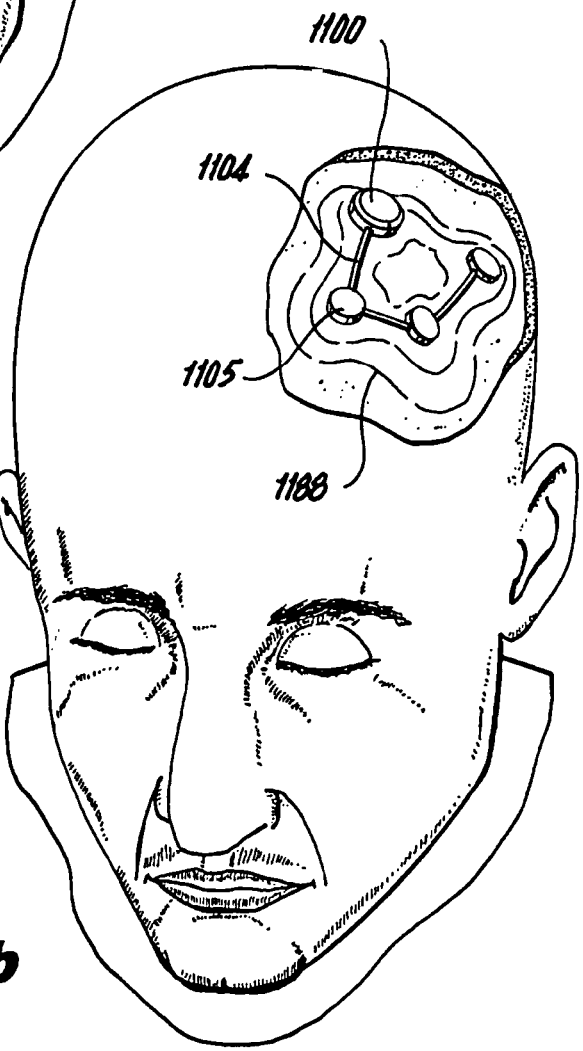
FIG. 11b illustrates networked neurostimulators in accordance with the invention, wherein satellite neurostimulators and/or electrodes are physically arranged in series to a controlling neurostimulator.

FIG. 11b illustrates networked neurostimulators 1100, 1105 connected in series and also arranged, for example, for premotor stimulation. The controlling neurostimulator 1100 is connected via a conductor lead 1104 to companion neurostimulators 1105. As described above, the connection can be such that it provides power and/or a controlling signal from the controlling neurostimulator to the companion neurostimulator(s). The representative electrical field lines 1188 in FIG. 11b represent a superposition of the individual electric fields generated by each neurostimulator when simultaneously activated. Such an arrangement can be useful when it is desirable to stimulate a large area of the brain simultaneously.

It should be noted that although the companion neurostimulators 1105 are physically connected in series to the controlling neurostimulator 1100, they can be configured and adapted to function independently or jointly in accordance with a prescribed protocol, for example by receiving and responding only to signals intended only for that particular companion neurostimulator by way of a purpose-built electronic circuit, for example. Moreover, the conducting lead can have a plurality of mutually isolated conductors therein, for delivering signals to selected companion neurostimulators.

Figures 11C, 11D:
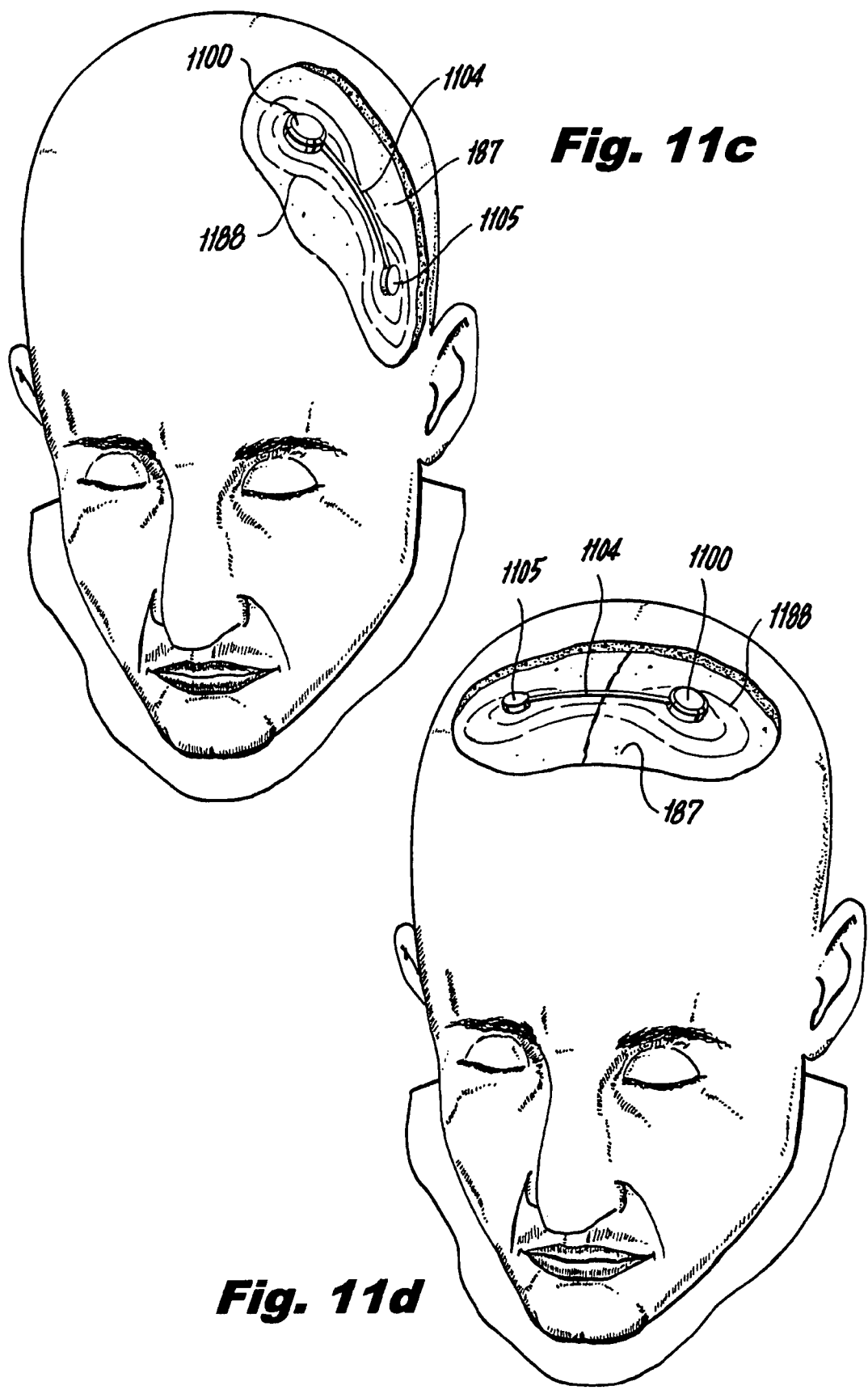
FIG. 11c illustrates networked neurostimulators in accordance with the invention, wherein a satellite neurostimulator and/or electrode and a controlling neurostimulator are mutually connected and are arranged on the patient's brain to effect the premotor cortex and Broca's area.
FIG. 11d illustrates networked neurostimulators in accordance with the invention, wherein a satellite neurostimulator and/or electrode and a controlling neurostimulator are mutually connected and are arranged on the patient's brain for stimulation of the premotor area on one side and motor cortex on the other side.

FIG. 11c illustrates a controlling neurostimulator 1100 and companion neurostimulator 1105 arranged for stimulation of the premotor cortex and Broca's area, for example. This arrangement is advantageous, because patients with strokes in the dominant hemisphere can simultaneously have motor weakness and language impairment. As with the foregoing embodiments, the neurostimulators can be connected by way of a conductive lead 1104. As illustrated, example electric field lines 1188 are provided to illustrate the extent of stimulation when the controlling stimulator 1100 and companion neurostimulator 1105 release a therapeutic electrical impulse simultaneously.

FIG. 11d illustrates a controlling neurostimulator 1100 and companion neurostimulator 1105 arranged for bilateral or "contralateral" premotor stimulation, for example. A treatment protocol where corresponding regions are treated simultaneously can enhance recovery. Motor recovery may be hampered by the increase of inhibitory influence of the contralateral hemisphere. Therefore, this inhibitory influence may be required (disinhibition) to be inhibited for the recovery of ipsilateral motor weakness from stroke.

Figure 12B:
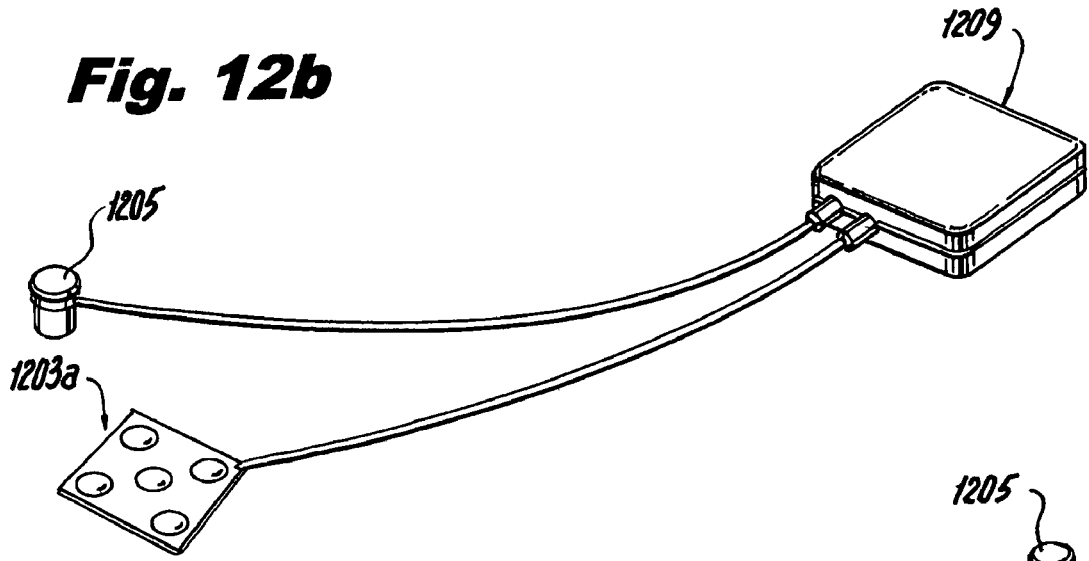
FIG. 12b illustrates networked neurostimulators in accordance with the invention, wherein a remotely situated control unit, which can include a pulse generator and additionally can include electrodes, is connected to a plurality of additional electrodes for evoking a motor evoked potential (MEP) and for providing therapeutic electrical field, respectively.
Figure 12C:
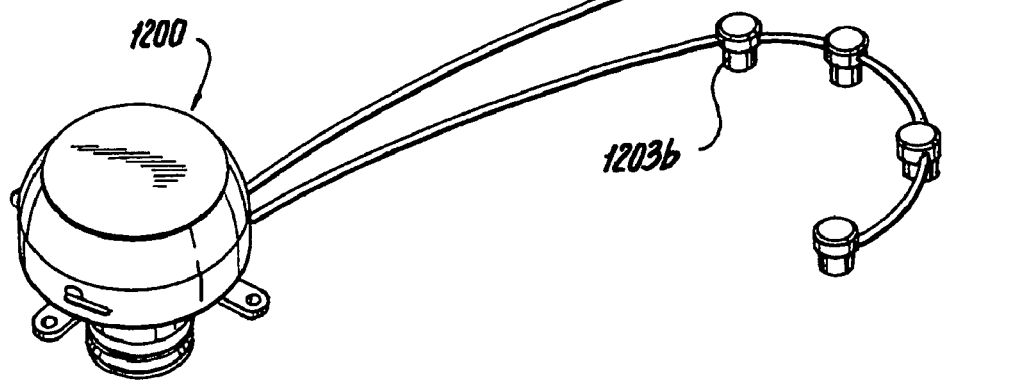
FIG. 12c illustrates networked neurostimulators in accordance with the invention, wherein a controlling neurostimulator is connected to a plurality of electrodes, which can be controlled by two or more independent control channels.

Advantageously, the systems of FIGS. 12a-12c can be used for treatment to enhance recovery following brain injury. As illustrated in FIG. 12a, the systems of FIGS. 12b-12d, as well as other embodiments set forth herein, can be configured and adapted to calibrate a treatment regimen by measuring brain excitability prior to treatment. As illustrated, the satellite electrode is arranged on the motor cortex, while the other stimulating electrode(s) is (are) arranged elsewhere on the brain. To measure brain excitability, the satellite electrode 1205 releases an electric impulse, which then evokes a motor response, which is measured by electrode 1287, arranged on the patient's hand, for example at the first digital interosseous muscle, which procedure is carried out before delivering the main stimulation. Following stimulation for determined periods of time, the motor evoked potential (MEP) can then be measured again. Comparison of MEP before and after the stimulation can provide a gauge to the physician as to how much stimulation by the electrode(s) 1203a will be necessary to achieve the desired results. Naturally, the satellite electrode 1205 may include a shape and attachment means to the cranium, as described hereinabove in connection with neurostimulators.

FIG. 12b illustrates a networked neurostimulation system in accordance with the invention, which has not been implanted. The system includes a surgically-implantable remote power and pulse generator or control unit 1209, a stimulating electrode array 1203a, including a plurality of contacts, and a satellite electrode 1205. The stimulating electrode array can be replaced by one or more neurostimulators having a configuration set forth herein, if desired, and as will be seen in connection with following embodiments. The satellite electrode is usually placed on the motor cortex and delivers electrical impulse to evoke a motor response in the corresponding extremity. The companion neurostimulator can be of a conventional design or can be constructed in accordance with any of the foregoing embodiments, for example, but in which the necessary circuitry and power source is provided in the separate control unit 1209. In such an embodiment, the control unit 1209 is preferably surgically implanted in the same location, as would be a conventional pacemaker.

FIG. 12c illustrates a further embodiment of a networked neurostimulation system in accordance with the invention. In this embodiment, the controlling neurostimulator 1200 includes the necessary power supply and componentry to control the companion neurostimulators 1203b and the satellite electrode 1205. Preferably, these two sets of components branching off of the controlling neurostimulator 1200, are connected to two separate channels of the controlling neurostimulator 1200 for independent operation.

Figure 12D:
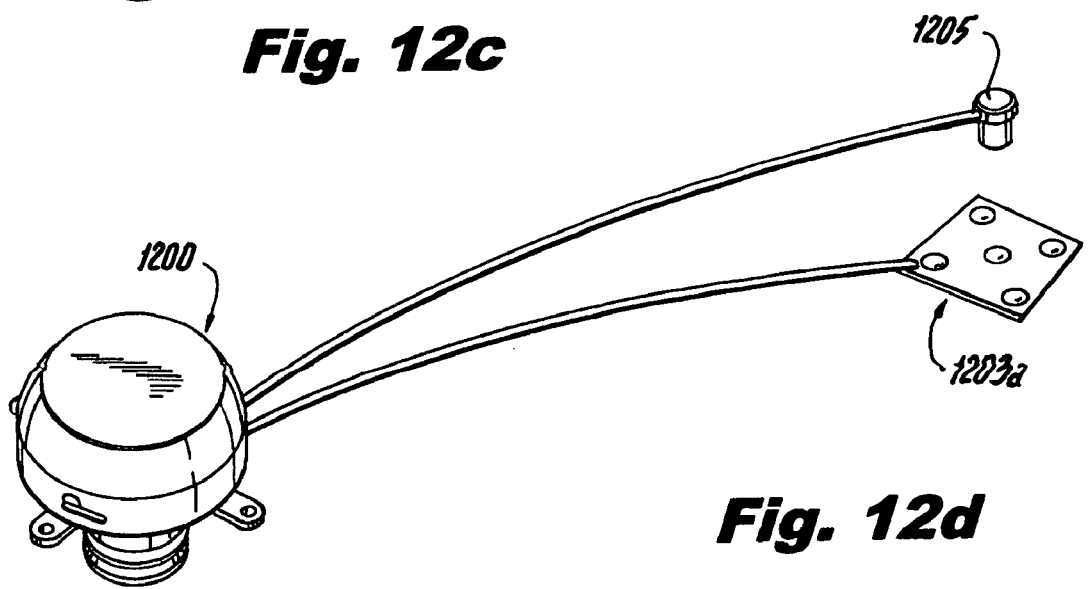
FIG. 12d illustrates another embodiment of networked neurostimulators in accordance with the invention, wherein a controlling neurostimulator is connected to a plurality of electrodes, which can also be controlled by two or more independent control channels.

FIG. 12d illustrates an embodiment of yet another system in accordance with the invention that essentially combines features of the embodiments of FIG. 12b and FIG. 12c. A controlling neurostimulator 1200 is provided in conjunction with an array 1203a, and a satellite electrode 1205, which can be, more particularly, a neurostimulator as set forth above, or of another design.

Figures 13A, 13B:
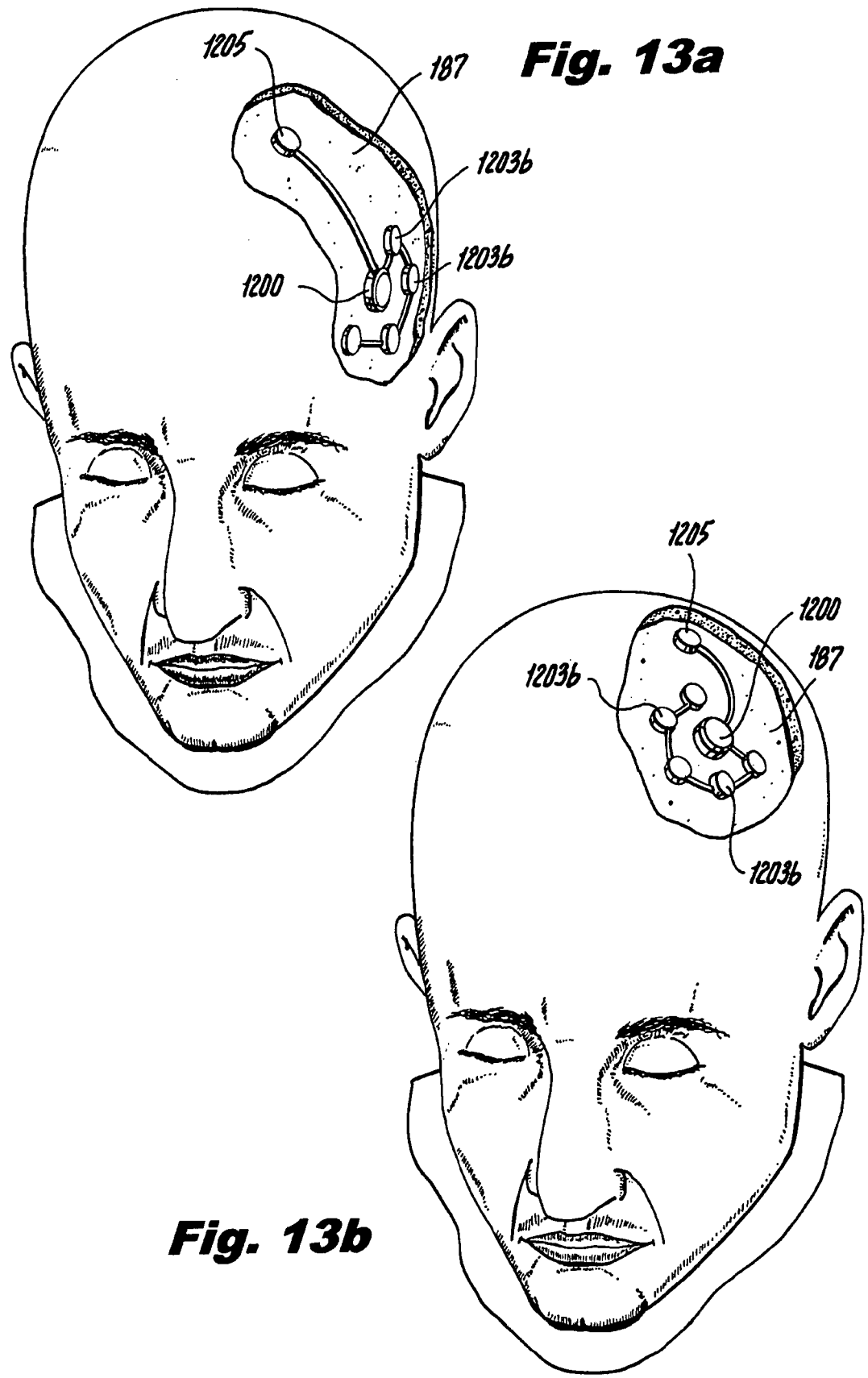
FIGS. 13a and 13b illustrate further embodiments of networked neurostimulators in accordance with the invention, wherein a controlling neurostimulator is connected to a plurality of electrodes or neurostimulators, which can be controlled by two or more independent control channels.

FIGS. 13a and 13b illustrate example arrangements for inhibiting temporal lobe epilepsy (FIG. 13a) and frontal lobe epilepsy (FIG. 13b), respectively. A controlling neurostimulator 1200 is used to control companion neurostimulators 1203b and the satellite electrodes 1205. Similarly, a sensor, such as sensor 1287, connected to relevant analytical equipment can be used to calibrate treatment protocol for a patient, as illustrated in FIG. 12a.

The invention also, therefore, includes a method for using motor evoked potential (MEP) for determination of optimal treatment parameters. In accordance with one embodiment, the invention includes the steps of:

1.) Implanting a primary stimulating electrode in a target region of the brain cortex, in which treatment is desired. Such primary stimulating electrode can be any of the aforementioned neurostimulators, for example.
2.) Implanting a satellite stimulating electrode arranged on the motor cortex of the patient's brain. Such satellite stimulating electrode, similarly, can be of a construction set forth herein.
3.) Stimulating the motor cortex a first time by way of the satellite stimulating electrode and measuring a motor evoked potential (MEP) at a muscle corresponding to the stimulated region of the motor cortex. Such muscle can be, for example, the first digital interosseous muscle.
4.) Stimulating the target region of the brain by way of the primary stimulating electrode.
5.) Stimulating the motor cortex a second time by way of the satellite stimulating electrode and measurement of motor evoked potential (MEP) at the muscle corresponding to the stimulated region of the motor cortex.
6.) Comparing the cortical excitability between the first motor cortex stimulation (before target region stimulation) and the second motor cortex stimulation (after target region stimulation).
7.) Determining optimal treatment parameters based on the compared cortical excitability.
8.) Stimulating the target region by way of the primary stimulating electrode for a treatment duration. The treatment may be prolonged or applied cyclically, depending on the determined optimal treatment parameters.

If desired, the steps 3 through 7 can be repeated at intervals during treatment, and/or following treatment to evaluate improvement and/or to modify treatment parameters.

Figure 14A:
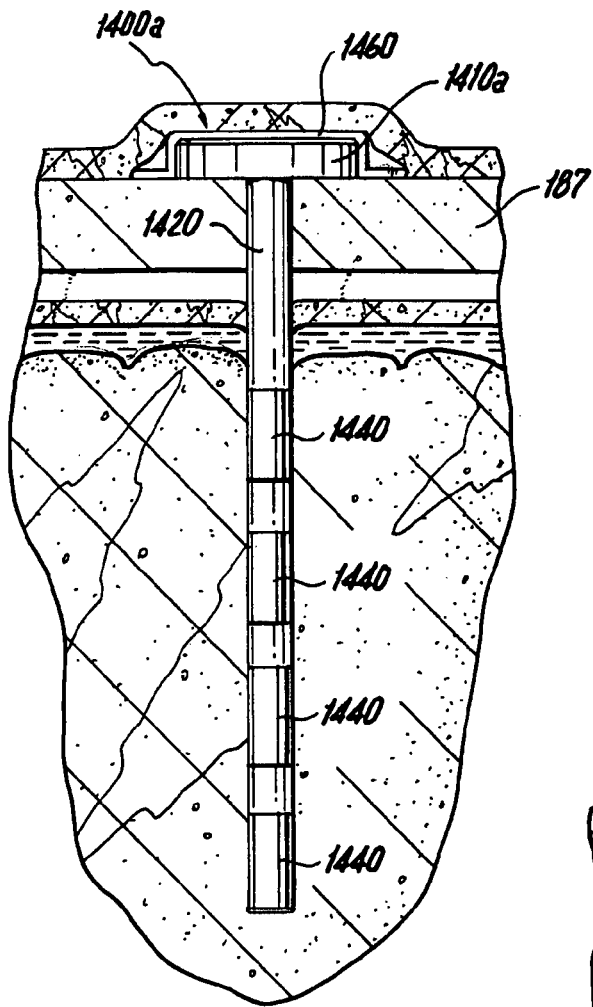
FIGS. 14a and 14b illustrate relatively long electrodes, in depth, in accordance with the invention that are particularly advantageous for stimulating regions deeper within the brain than the cerebral cortex.
Figure 14B:
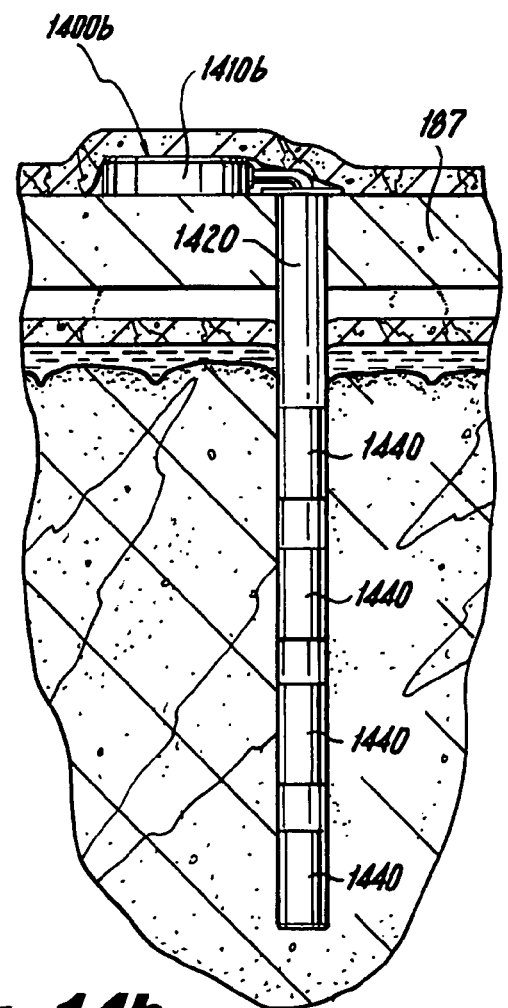

In accordance with still a further aspect of the present invention, neurostimulators for implantation within and treatment of deeper regions of the brain are provided. FIGS. 14a and 14b illustrate neurostimulators 1400a, 1400b, respectively for extending into the brain for more direct treatment of deeper lying neural tissue than possible by superficial cortical stimulation. A disorder requiring treatment with such a device may be, for example, medial temporal lobe epilepsy.

As illustrated, each neurostimulator 1400a, 1400b includes a housing 1410a, 1410b adapted and configured to enclose the necessary componentry for operation, as described in connection with other embodiments of neurostimulators hereinabove. Either neurostimulator can be provided with anchoring capability, such as a strap 1460. Moreover, each neurostimulator includes a body portion 1420, on which electrodes 1440 are placed along its length, which is, in one embodiment about 45 mm. The electrodes 1440 may be unipolar or bi-polar. That is, they may have the same polarity, with an opposite pole being located remotely or at the housing 1410a, 1410b of the neurostimulator 1400a, 1400b. Alternatively, they may include electrodes 1440 of different polarities, such as polarities that alternate along the length of the body 1420.

While the apparatus and methods of subject invention have been shown and described with reference to preferred embodiments, those skilled in the art will readily appreciate that changes and/or modifications may be made thereto without departing from the spirit and scope of the subject disclosure. For example, it should be understood that features described in connection with one embodiment may equally be applied to other embodiments, even though not directly described in connection with such other embodiments.

We claim:

1. An implantable neurostimulator comprising:
    a housing;
    mounting means for securing the housing and the neurostimulator to a cranium of a patient;
    stimulus generating means provided within the housing for generating a therapeutic electrical stimulus;
    an electrode for contacting a dura of a brain of the patient;
    biasing means arranged between the mounting means and the electrode for biasing the electrode toward the brain of the patient and moving the electrode independent of the housing;
    a wire electrically connecting the pulse generating means and the electrode wherein the pulse generating means is housed in the housing mounted to the patient's cranium and the electrode is biased against the patient's brain via the biasing means, the wire adapted and configured to deliver the electrical stimulus generated by the pulse generating means to the electrode; and
    a stem element extending integrally from the housing and arranged between the housing and the electrode, a length of the stem setting a minimum distance between the housing and the electrode.

2. The implantable neurostimulator of claim 1, further comprising an antenna operatively connected to the pulse generating means, the pulse generating means receiving a control signal from an external control unit through the antenna.

3. The implantable neurostimulator of claim 1, wherein the biasing means is arranged between the housing and the electrode.

4. The implantable neurostimulator of claim 1, wherein the biasing means is a resilient element.

5. The implantable neurostimulator of claim 4, wherein the biasing means is a spring.

6. The implantable neurostimulator of claim 4, wherein the biasing means functions as the electrically conductive element by having at least an electrically conductive portion.

7. The implantable neurostimulator of claim 1, wherein the biasing means is one or more shims.

8. The implantable neurostimulator of claim 1, wherein the mounting means is integrally formed with the housing.

9. The implantable neurostimulator of claim 8, wherein the mounting means includes one or more extension portions extending from the housing, adapted and configured to be secured to the cranium of the patient by one or more mechanical fasteners.

10. The implantable neurostimulator of claim 1, wherein the mounting means is integrally formed with the stem element, the stem element directly engaging the cranium of the patient.

11. The implantable neurostimulator of claim 10, wherein the mounting means includes threads arranged on an outer surface of the stem element for engaging the cranium of the patient.

12. The implantable neurostimulator of claim 10, wherein the mounting means includes a textured surface arranged on an outer surface of the stem element for engaging the cranium of the patient.

13. The implantable neurostimulator of claim 12, wherein the textured surface is adapted and configured to promote bone ingrowth into the neurostimulator, to aid fastening of the neurostimulator to the cranium.

14. The implantable neurostimulator of claim 1, wherein the mounting means includes a fastening strap adapted and configured to engage the housing and to be secured to the cranium of the patient by one or more mechanical fasteners.

15. The implantable neurostimulator of claim 1, wherein the mounting means includes a platform element configured and adapted to be secured to the cranium of the patient by one or more mechanical fasteners, to which the stem element is also mutually engageable.

16. The implantable neurostimulator of claim 1, wherein the stem element functions as the electrically conductive element by having at least an electrically conductive portion.

17. The implantable neurostimulator of claim 1, wherein the housing includes a cap portion and a base portion sealed together, forming the housing.

18. The implantable neurostimulator of claim 1, further comprising a retainer lip arranged on a lower surface of the housing, adapted and configured to engage the stem element.

19. The implantable neurostimulator of claim 18, wherein the retainer lip includes an anti-rotation feature to inhibit relative rotation between the retainer lip and the stem element.

20. The implantable neurostimulator of claim 1, wherein the housing is adapted and configured to function as a second electrode, to complete an electrical circuit with the first electrode when delivering a therapeutic electrical stimulus.

21. The implantable neurostimulator of claim 1, wherein the housing is provided with a separate second electrode, carried thereon, to complete an electrical circuit with the first electrode when delivering a therapeutic electrical stimulus.

22. The implantable neurostimulator of claim 1, wherein the first electrode is adapted and configured to slideably engage the stem element, a biasing element being provided between the electrode and stem element for urging the first electrode toward the brain of the patient.

23. The implantable neurostimulator of claim 22, wherein the stem element is provided with a groove for engaging the biasing element, to prevent unintentional relative translation between the stem element and the biasing element.

24. The implantable neurostimulator of claim 1, further comprising an aperture defined in the housing, configured and adapted to receive passage of an antenna, extending from the stimulus generating means outside of the housing.

25. The implantable neurostimulator of claim 24, wherein a feedthrough element is provided within the aperture to seal an internal environment of the housing from the external environment of the housing.

26. The implantable neurostimulator of claim 1, further comprising an aperture defined in the housing, configured and adapted to receive passage of a conductor, extending from the stimulus generating means to the first electrode.

27. A system for therapeutic neurostimulation, the system comprising: a) a plurality of implantable neurostimulators in accordance with claim 1; and b) communication means connecting the plurality of neurostimulators.

28. The system for therapeutic neurostimulation of claim 27, wherein the plurality of implantable neurostimulators are arranged in an array in the cranium of the patient.

29. The system for therapeutic neurostimulation of claim 28, wherein the array is a rectangular array.

30. The system for therapeutic neurostimulation of claim 27, wherein the array is a circular array.

31. The system for therapeutic neurostimulation of claim 27, wherein the plurality of implantable neurostimulators are adapted and configured to communicate with one another by way of a conductive element provided between implantable neurostimulators.

32. The system for therapeutic neurostimulation of claim 7, wherein the plurality of implantable neurostimulators are adapted and configured to communicate with one another by way of a wireless signal.

33. The system for therapeutic neurostimulation of claim 27, wherein at least one implantable neurostimulator is adapted and configured to receive power from at least one other implantable neurostimulator by way of a conductive element provided between implantable neurostimulators.

34. The system for therapeutic neurostimulation of claim 27, further comprising a programmer provided external to the patient for programming a predetermined treatment protocol into at least one of the implantable neurostimulators.

35. The implantable neurostimulator of claim 1 further including a programming unit remotely located and coupled to the stimulus generating means operative to control the stimulus generating means and provide an inductive charge to the stimulus generating means.

* * * * *